US012037322B2

(12) United States Patent
Carson et al.

(10) Patent No.: US 12,037,322 B2
(45) Date of Patent: Jul. 16, 2024

(54) AHR AGONISTS

(71) Applicant: Eli Lilly and Company, Indianapolis, IN (US)

(72) Inventors: Cheryl Ann Carson, Indianapolis, IN (US); Christian Alexander Clarke, Fishers, IN (US); Douglas Linn Gernert, Fishers, IN (US); Steven James Green, Indianapolis, IN (US); William Glen Holloway, Martinsville, IN (US); David Gene Barrett, Zionsville, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 17/943,573

(22) Filed: Sep. 13, 2022

(65) Prior Publication Data
US 2023/0127797 A1    Apr. 27, 2023

Related U.S. Application Data

(60) Provisional application No. 63/261,129, filed on Sep. 13, 2021.

(51) Int. Cl.
| | | |
|---|---|---|
| *C07D 401/12* | (2006.01) | |
| *C07D 215/54* | (2006.01) | |
| *C07D 413/12* | (2006.01) | |
| *C07D 417/12* | (2006.01) | |
| *C07D 471/04* | (2006.01) | |
| *C07D 491/052* | (2006.01) | |

(52) U.S. Cl.
CPC ......... *C07D 401/12* (2013.01); *C07D 215/54* (2013.01); *C07D 413/12* (2013.01); *C07D 417/12* (2013.01); *C07D 471/04* (2013.01); *C07D 491/052* (2013.01)

(58) Field of Classification Search
CPC .. C07D 401/12; C07D 215/20; C07D 403/12; C07D 413/12; C07D 211/88; C07D 417/12; C07D 471/04; A61K 31/427; A61K 31/433; A61K 31/444; A61K 31/517
See application file for complete search history.

(56) References Cited

U.S. PATENT DOCUMENTS

2009/0325948 A1   12/2009   Hurley et al.

FOREIGN PATENT DOCUMENTS

| EP | 0059698 | 9/1982 |
|---|---|---|
| EP | 3026045 | 6/2016 |
| EP | 3067356 | 9/2016 |
| WO | 01/30758 | 5/2001 |
| WO | 2008/014307 | 1/2008 |
| WO | 2013/144231 | 10/2013 |
| WO | 2016049097 | 3/2016 |

OTHER PUBLICATIONS

Lin et al., An overview of aryl hydrocarbon receptor ligands in the last two decades (2002-2022): A medicinal chemistry perspective, European Journal of Medicinal Chemistry 244 (2022) 114845, pp. 1-20.*
Ehrlich, et al., "Is chronic AhR activation by rapidly metabolized ligands safe for the treatment of immune-mediated diseases?", Current Opinion in Toxicology, vol. 2, pp. 72-78 (2017).
Rothhammer, et al., "The aryl hydrocarbon receptor: an environmental sensor integrating immune responses in health and disease," Nat. Rev. Immunol., vol. 19, pp. 184-197 (2019).
Kerkvliet, et al., "Activation of aryl hydrocarbon receptor by TCDD prevents diabetes in NOD mice and increases Foxp3+ T cells in pancreatic lymph nodes," Immunotherapy, vol. 1, No. 4, pp. 539-547 (2009).
Quintana, et al., "Control of $T_{reg}$ and $T_H17$ cell differentiation by the aryl hydrocarbon receptor," Nature, vol. 453, pp. 65-71 (2008).
Zhang, et al., Invest. Opthalmol. Vis. Sci., vol. 51, pp. 2109-2117 (2010).
Takamura, et al., "Activation of the aryl hydrocarbon receptor pathway may ameliorate dextran sodium sulfate-induced colitis in mice," Immunology and Cell Biology, vol. 88, pp. 685-689 (2010).
Benson, et al., "Aryl Hydrocarbon Receptor Activation by TCDD Reduces Inflammation Associated with Crohn's Disease," Toxicological Sciences, vol. 120, No. 1, pp. 68-78 (2010).
Singh, et al., "Activation of Aryl Hydrocarbon Receptor (AhR) Leads to Reciprocal Epigenetic Regulation of FoxP3 and IL-17 and Expression and Amelioration of Experimental Colitis," PLoS One, vol. 6, No. 8, p. e23522 (2011).
Pauly, et al., "The Aryl Hydrocarbon Receptor Influences Transplant Outcomes in Response to Environmental Signals," Toxicol. Environ. Chem., vol. 94, No. 6, pp. 1175-1187 (2012).
Schulz, et al., "Activation of the Aryl Hydrocarbon Receptor Suppresses Sensitization in a Mouse Peanut Allergy Model," Toxicological Sciences, vol. 123, No. 2, pp. 491-500 (2011).
Li, et al., "TCDD-Induced Activation of Aryl Hydrocarbon Receptor Inhibits Th17 Polarization and Regulates Non-Eosinophilic Airway Inflammation in Asthma," PLoS One, vol. 11, p. e0150551 (2016).
Luebke, et al., "Suppression of Allergic Immune Responses to House Dust Mite (HDM) in Rats Exposed to 2,3,7,8-TCDD," Toxicological Sciences, vol. 62, pp. 71-79 (2001).
Ukrainets, et al., "4-Hydroxy-2-quinolones. 95*. Synthesis, structure, and antitubercular properties of hetarylamides of 4-hydroxy-2-oxo-1,2,5,6,7,8-hexahydroquinoline-3-carboxylic acid," Chemistry of Heterocyclic Compounds, vol. 42, No. 6, pp. 765-775 (2006).
Li Lin, et al. "An overview of aryl hydrocarbon receptor ligands in the last two decades (2002-2022): A medicinal chemistry perspective," European Journal of Medicinal Chemistry, vol. 244, pp. 1-20 (2022).

(Continued)

*Primary Examiner* — Deepak R Rao
(74) *Attorney, Agent, or Firm* — Shenshen Li

(57) ABSTRACT

The present invention relates to certain substituted AHR agonist compounds, to pharmaceutical compositions comprising the compounds and to methods of using the compounds to treat immune-mediated diseases.

17 Claims, No Drawings

(56) References Cited

OTHER PUBLICATIONS

Manera, et al., "Rational Design, Synthesis, and Pharmacological Properties of New 1,8-Naphthyridin-2(1H)-on-3-Carboxamide Derivatives as Highly Selective Cannabinoid-2 Receptor Agonists," J. Med. Chem, vol. 52, pp. 3644-3651 (2009).
Manera, et al. "New quinolone- and 1,8-naphthyridine-3-carboxamides as selective CB2 receptor agonists with anticancer and immune-modulatory activity," European Journal of Medicinal Chemistry, vol. 97, pp. 10-18 (2015).
Lucchesi, et al., "CB2-Selective Cannabinoid Receptor Ligands: Synthesis, Pharmacological Evaluation, and Molecular Modeling Investigation of 1,8-Naphthyridin-2(1H)-one-3-carboxamides," Journal of Medicinal Chemistry, vol. 57, pp. 8777-8791 (2014).

\* cited by examiner

AHR AGONISTS

The present invention relates to novel AHR agonist compounds, to pharmaceutical compositions comprising the compounds and to methods of using the compounds to treat certain physiological disorders.

The present invention is the field of treatment of certain immune-mediated diseases (IMD), in particular psoriasis, via the activation of the aryl hydrocarbon receptor (AHR).

IMDs encompass a broad range of chronic and debilitating inflammatory conditions that affect approximately 4% of the population worldwide. In view of the limited efficacy of currently available treatments, there is significant unmet need for potent, selective, and safe drugs for the treatment of IMDs.

AHR is a transcription factor which regulates many aspects of immunological function, most notably the suppression of adaptive immune responses (Ehrlich et al., *Curr. Opin. Toxicol.*, 2, 72-78 (2017)). Prototypical AHR agonists include halogenated dibenzodioxins, such as 2,3,7,8-tetrachlorodibenzodioxin (TCDD), tryptophan metabolites, such as L-kynurenine, bilirubin and PGE2. Results from studies on AHR agonists, especially TCDD, suggest that immune suppression occurs as the result of AHR-induced expression of regulatory T cells (Tregs), TH17 cells and dendritic cells (DCs) (Rothhammer et al., *Nat. Rev, Immunol.*, 19, 184-197 (2019)). TCDD has been shown to be effective in the prevention of several murine models of NID, including type-1 diabetes (Kerkvliet et al., *Immunotherapy,* 1, 539-547 (2009)), autoimmune encephalomyelitis (Quintana et al., *Nature,* 453, 65-71, (2008)), autoimmune uveoretinitis (Zhang et al., *Invest. Opthalmol. Vis. Sci.,* 51, 2109-2117 (2010)), inflammatory bowel disease (Takamura et al., *Immunol. Cell. Biol.,* 88, 685-689 (2010), Benson et al., *Toxicol. Sci.,* 120, 68-78 (2011), Singh et al., *PLoS One,* 6(8), e23522 (2011)), as well as several models of transplant tolerance (Pauly at al., *Toxicol. Environ. Chem.,* 94, 1175-1187 (2012)) and allergic diseases (Schulz et al., *Toxicol. Sci.,* 123, 491-500 (2011), Li et al, *PLoS One,* 11, e0150551 (2016), Luebke et al., *Toxicol. Sci.,* 62, 71-79 (2001)).

AHR also regulates the expression of CYP1A1, CYP1A2 and CYP1B1, which catalyze the metabolism of polycyclic aromatic hydrocarbon (PAH) and other aromatic compounds (e.g., estrogen). While in some cases (for example in the case of beno[a]pyrene) this metabolism results in the formation of reactive species, CYP induction is also believed to be critical for the detoxification and metabolic clearance of PAHs, which reduces the probability of bioactivation, and DNA adduct formation. Several marketed drugs were found to activate AHR (thus upregulating CYP1A1, CYP1A2 and CYP1B1) after their FDA approval, yet their long-term use is not associated with dioxin-like toxicities (Ehrlich et al., *Curr. Opin. Toxicol.,* 2, 72-78 (2017)). As such, CYP induction is no longer viewed as a barrier to the adoption of AHR agonists in therapy (Ehrlich et al., *Curr. Opin. Toxicol.,* 2, 72-78 (2017)).

The bacterial stilbenoid DMVT-505 (tapinarof) formulated as a 1% topical cream, is currently undergoing Phase 3 clinical trials for the treatment of plaque psoriasis in adults (NCT04053387). Despite this, there remains a need for novel oral, selective and potent AHR agonists for the treatment of IMDs.

Ukrainets, I. V., et. al., *Chemistry of Heterocyclic Compounds,* 42(6), 2006, 765-775 discloses certain 4-hydroxy-2-oxo-5,6,7,8-tetrahydro-1H-quinoline-3-carboxamide compounds with antibacterial properties. US 2009/0325948 A1 discloses certain cycloalkyl-fused 4-hydroxy-2-oxo-1H-pyridine-3-carboxamide compounds which are inhibitors of bacterial undecaprenyl pyrophosphate synthase (UPPS).

The present invention provides certain compounds that are agonists of AHR.

Accordingly, the present invention provides a compound of Formula I.

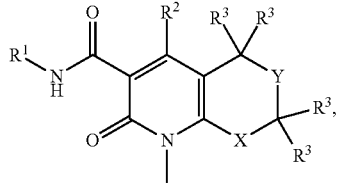

Formula I wherein,
R$^1$ is selected from phenyl, C$_1$-C$_6$ alkyl, C$_3$-C$_6$ cycloalkyl, 5- to 6-membered heteroaryl optionally substituted by 1 to 2 R$^i$ and 8- to 10-membered bicyclic heteroaryl optionally substituted with 1 to 2 R$^i$;

R$^2$ is selected from H and OH;

X is selected from bond, —C(R$^3$)$_2$— and —C(R$^3$)$_2$C(R$^3$)$_2$—;

Y is selected from —C(R$^3$)$_2$—, —O— and —N(R$^j$)—;

R$^3$ is independently selected from H and C$_1$-C$_3$ alkyl;

R$^i$ is selected from halogen, CH$_3$, OCH$_3$ and CF$_3$;

R$^j$ is C$_1$-C$_3$ alkyl, or a pharmaceutically acceptable salt thereof.

The present invention also provides a compound of Formula I, wherein R$^1$ is selected from phenyl and 5- to 6-membered heteroaryl optionally substituted with 1 to 2 R$^i$, or a pharmaceutically acceptable salt thereof.

The present invention further provides a compound of Formula I, wherein Y is —C(R$^3$)$_2$—, or a pharmaceutically acceptable salt thereof.

The present invention also provides a compound of Formula I, wherein R$^3$ is independently selected from H, CH$_3$, CH$_2$CH$_3$ and CH(CH$_3$)$_2$ or a pharmaceutically acceptable salt thereof.

The present invention provides a compound of Formula I, wherein X is bond, or a pharmaceutically acceptable salt thereof.

The present invention further provides a compound of Formula I, which is selected from:

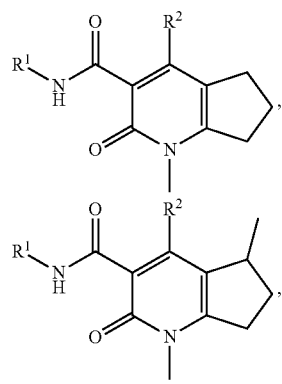

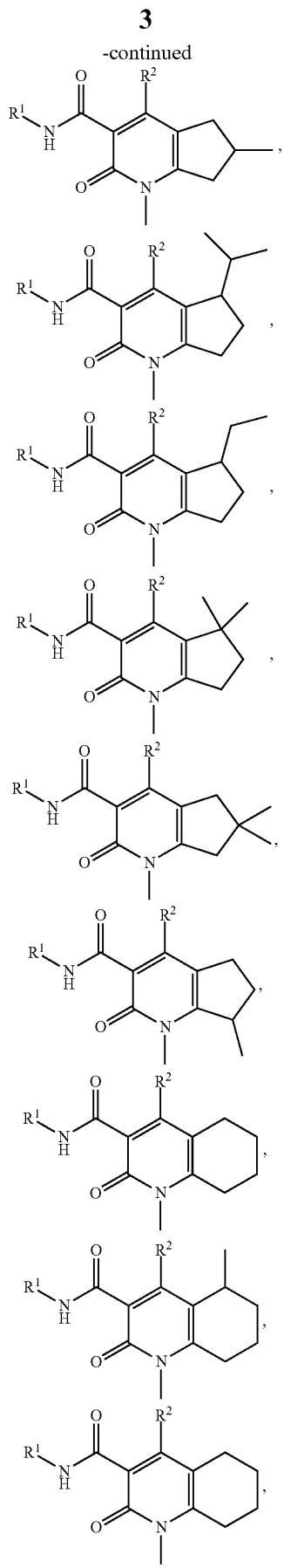
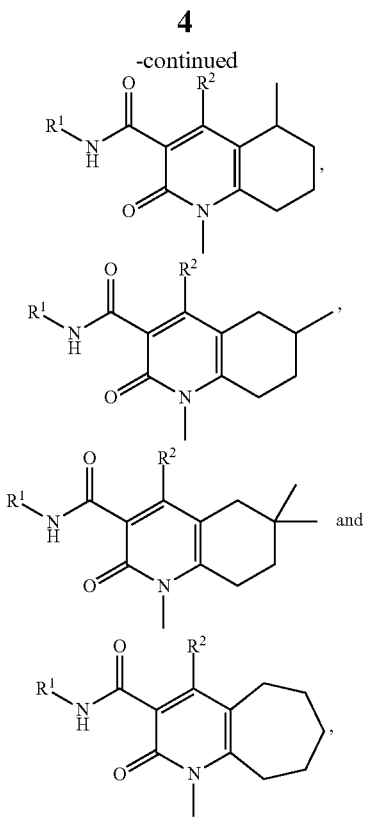
or a pharmaceutically acceptable salt thereof.
The present invention provides a compound of Formula I, which is selected from:
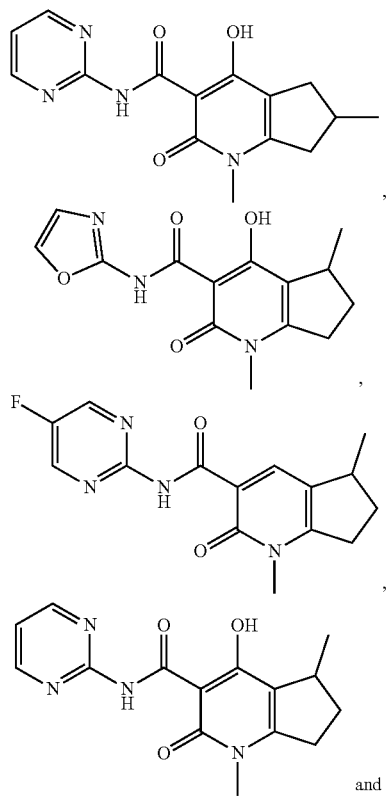

-continued

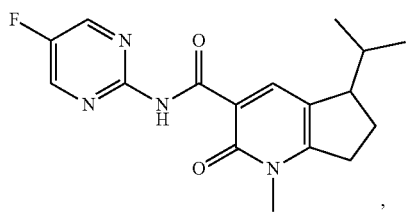

or a pharmaceutically acceptable salt thereof.

The present invention also provides a compound of Formula I, which is selected from:

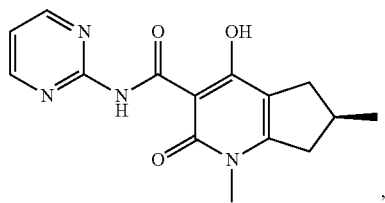

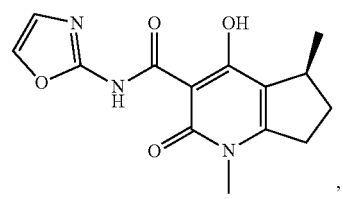

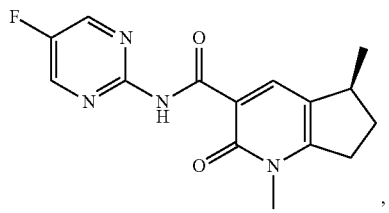

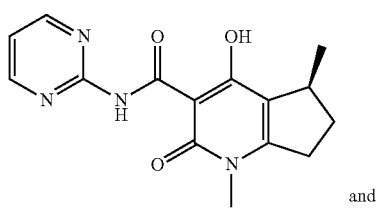

and

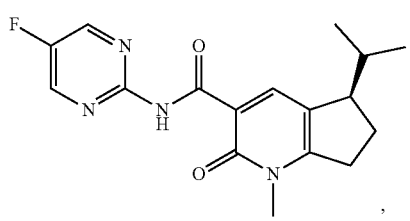

or a pharmaceutically acceptable salt thereof.

The present invention further provides a compound of Formula I, which is selected from:

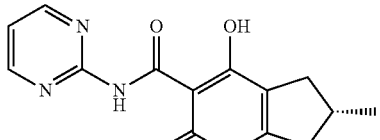

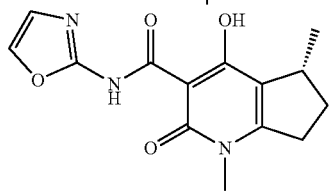

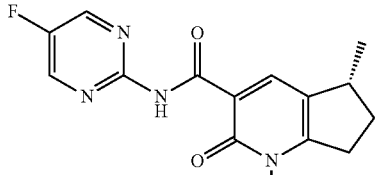

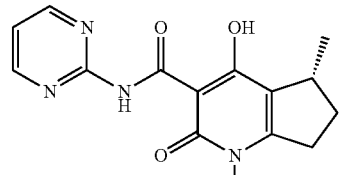

and

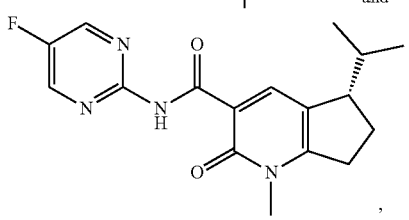

or a pharmaceutically acceptable salt thereof.

The present invention also provides a compound of Formula I according to any of the above embodiments as the free base.

The present invention further provides pharmaceutical composition, comprising a compound or a pharmaceutically acceptable salt thereof according to any of the above embodiments with one or more pharmaceutically acceptable carriers, diluents, or excipients.

The present invention provides a method of treating an immune-mediated disease in a patient, comprising administering to a patient in need of such treatment an effective amount of a compound, or pharmaceutically acceptable salt thereof, or composition according to any of the above embodiments.

The present invention also provides a method of treating a disease or disorder selected from psoriasis, ulcerative colitis, Crohn's disease, graft-versus-host disease, and multiple sclerosis in a patient, comprising administering to a patient in need of such treatment an effective amount of a compound, or pharmaceutically acceptable salt thereof, or composition according to any of the above embodiments.

The present invention provides a compound according to any of the above embodiments, or a pharmaceutically acceptable salt thereof, for use in therapy.

The present invention also provides a compound according to any of the above embodiments, or a pharmaceutically acceptable salt thereof, for use in the treatment of a disease or disorder selected from psoriasis, ulcerative colitis, Crohn's disease, graft-versus-host disease, and multiple sclerosis.

Furthermore, the present invention provides a compound according to any of the above embodiments, or a pharmaceutically acceptable salt thereof, for the manufacture of a medicament for the treatment of an immune-mediated disease. In addition, the present invention provides a compound according to any of the above embodiments, or a pharmaceutically acceptable salt thereof, for the manufacture of a medicament for the treatment of a disease or disorder selected from psoriasis, ulcerative colitis, Crohn's disease, graft-versus-host disease, and multiple sclerosis.

As used herein, the term "alkyl", used alone or as part of a larger moiety, refers to a saturated, straight or branched chain hydrocarbon group containing one or more carbon atoms.

As used herein, the term "cycloalkyl" refers to a saturated ring system containing at least three carbon atoms. Exemplary monocyclic cycloalkyl rings include cyclopropyl, cyclobutyl, cyclopentyl, cyclohexyl, and cycloheptyl.

As used herein, the term "heteroaryl" refers to groups having 5 to 10 ring atoms, preferably 5, 6, 9, or 10 ring atoms, having 6, 10, or 14 π-electrons shared in a cyclic array, and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl and pyrazinyl. The term "bicyclic heteroaryl" includes groups in which a heteroaryl ring is fused to one more aryl, or heteroaryl rings. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl and quinoxalinyl.

As used herein, the term "OR isomer" in combination with the terms "isomer 1" or "isomer 2" refers to compounds which possess a specific, but undetermined (either R or S), stereochemistry. The terms "isomer 1" and "isomer 2" denote either the R and S, or the S and R enantiomers of the same molecule.

As used herein, when X is a bond, the saturated ring is a 5-membered ring. When X is $CR^3$, the saturated ring is a 6-membered ring. When X is $CR^3$—$CR^3$, the saturated ring is a 7-membered ring.

As used herein, the term "immune-mediated disease" encompasses a group of autoimmune inflammatory disorders characterized by an alteration in cellular homeostasis. Immune-mediated diseases may be triggered by environmental factors, dietary habits, infectious agents, and genetic predisposition.

As used herein, the terms "treating" or "to treat" includes restraining, slowing, stopping, or reversing the progression or severity of an existing symptom or disorder.

As used herein, the term "patient" refers to a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by one skilled in the art by the use of known techniques. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.1 to about 15 mg/kg of body weight. In some instances, dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and transdermal routes. Most preferably, such compositions are for oral administration. Such pharmaceutical compositions and processes for preparing same are well known in the art (See, e.g., Remington: The Science and Practice of Pharmacy, A. Adejare, Editor, $23^{rd}$ Edition, Elsevier Academic Press, 2020).

The compounds of the present invention, or pharmaceutically acceptable salts thereof, may be prepared according to the following Preparations and Examples by methods well known and appreciated in the art. Suitable reaction conditions for the steps of these Preparations and Examples are well known in the art and appropriate substitutions of solvents and co-reagents are within the skill of the art. Likewise, it will be appreciated by those skilled in the art that synthetic intermediates may be isolated and/or purified by various well-known techniques as needed or desired, and that frequently, it will be possible to use various intermediates directly in subsequent synthetic steps with little or no purification. As an illustration, compounds of the preparations and examples can be isolated, for example, by silica gel purification, isolated directly by filtration, or crystallization. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, and is well appreciated by the skilled chemist. All substituents, unless otherwise indicated, are as previously defined, and all reagents are well known and appreciated in the art.

Certain abbreviations are defined as follows: "ACN" refers to acetonitrile; "BSA" refers to bovine serum albumin; "DCM" refers to dichloromethane; "DCE" refers to 1,2-dichloroethane; "DEA" refers to diethylamine; "DIPEA" refers to N,N-diisopropylethylamine; "DMEM" refers to Dulbecco's modified eagle medium; "DMF-DMA" refers to N,N-dimethylformamide dimethyl acetal; "DMF" refers to N,N-dimethylformamide; "DPBS" refers to Dulbecco's phosphate-buffered saline; "DMSO" refers to dimethyl sulfoxide; "EGFP" refers to enhanced green fluorescence protein; "ES/MS" refers to electrospray ionization/mass spectroscopy; "EtOAc" refers to ethyl acetate; "EtOH"

refers to ethanol or ethyl alcohol; "FBS" refers to fetal bovine serum; "HATU" refers to 1-[bis(dimethylamino) methylene]-1H-1,2,3-triazolo[4,5-b]pyridinium 3-oxide hexafluorophosphate; "h" refers to hour or hours; "IPA" refers to isopropyl alcohol or isopropanol; "MeOH" refers to methanol or methyl alcohol; "min" refers to minute or minutes; "MTBE" refers to methyl tert-butyl ether; "m/z" refers to mass to charge ratio; "NMI" refers to N-methylimidazole; "RT" refers to room, or ambient, temperature; "SFC" refers to supercritical fluid chromatography; "T3P" refers to propanephosphonic acid anhydride; "TCFH" refers to N,N,N',N'-tetramethylchloroformamidinium hexafluorophosphate; and "THF" refers to tetrahydrofuran.

In an optional step, a pharmaceutically acceptable salt of a compound according to any of the above embodiments can be formed by reaction of an appropriate free base of the compound with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). "Salt selection for basic drugs," *International Journal of Pharmaceutics*, 33: 201-217 (1986). One of ordinary skill in the art will appreciate that a compound according to any of the above embodiments is readily converted to and may be isolated as a pharmaceutically acceptable salt.

The compounds of Formula I or pharmaceutically acceptable salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formula I, or pharmaceutically acceptable salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art.

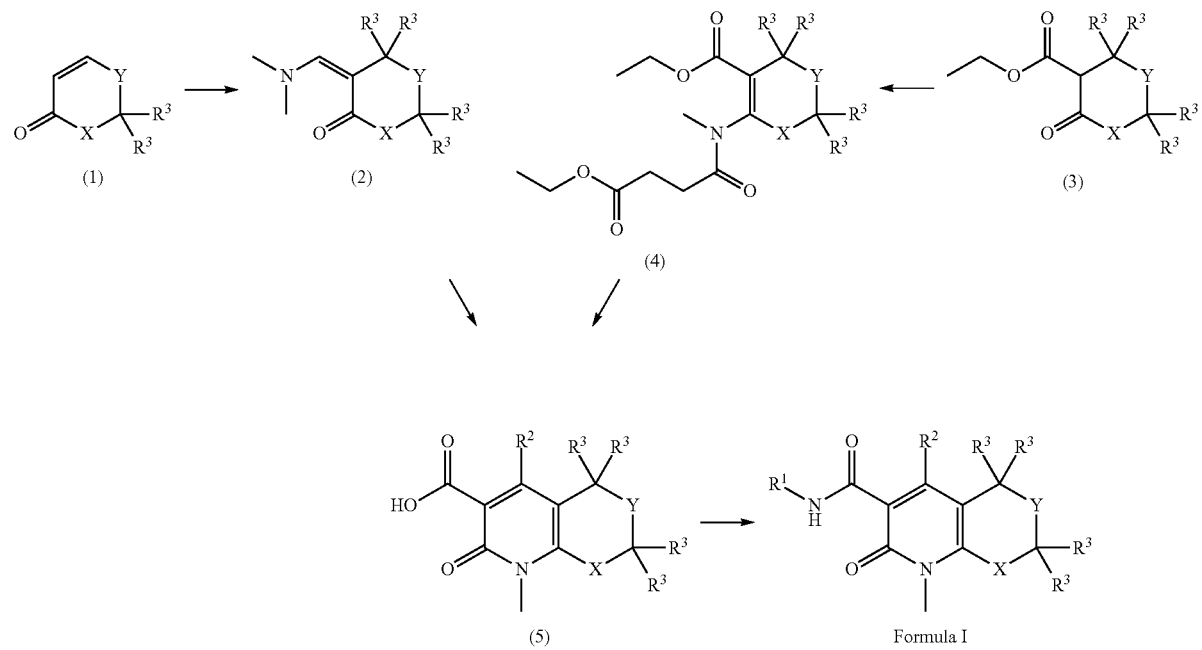

Scheme 1. General synthetic pathway for the preparation of compounds of Formula I Scheme 1 depicts the general preparation of the compounds of Formula I.

In a first alternative, an organic cuprate undergoes a 1,4-addition with unsaturated cyclic ketone (1). The intermediate enol is then trapped in situ with N,N-dimethylformamide dimethyl acetal to give intermediate (2). Subsequent cyclization of (2) with methyl cyanoacetate, followed by methylation with iodomethane and ester hydrolysis affords carboxylic acid intermediate (5).

In a second alternative, ketoester (3) is first reacted with methylamine to yield an enamine intermediate, which is then alkylated with 3-chloro-3-oxo-propanoate to afford intermediate (4). Intramolecular cyclization of (4) at elevated temperature using a base, followed by ester hydrolysis afford carboxylic acid intermediate (5).

Finally, carboxylic acid intermediate (5) is subjected to an amide coupling reaction to afford compounds of Formula I.

PREPARATIONS AND EXAMPLES

The following Preparations and Examples further illustrate the invention.

Preparation 1

1,5-dimethyl-2-oxo-6,7-dihydro-5H-cyclopenta[b]pyridine-3-carboxylic acid

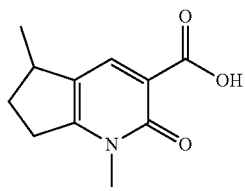

Step A: Cuprous iodide (56 g, 294 mmol) and tributylphosphine (150 mL, 570 mmol) is stirred in THF (300 mL) for 10 min under $N_2$. The mixture is cooled to −78° C. and methyllithium (1.6 mol/L in diethyl ether) (180 mL, 290 mmol) added dropwise. After complete addition, the mixture is stirred at −78° C. for 30 min under $N_2$. After this time boron trifluoride diethyl etherate (34 mL, 268.8 mmol) is added and stirred for 5 min, and cyclopent-2-en-1-one (20 g, 243.6 mmol) added. This mixture is stirred at −68° C. for 10 min, then warmed to −55° C., stirred for 20 min, warmed again to −40° C. and stirred for 10 min under $N_2$. DMF-DMA (81 mL, 607 mmol) is then added, and the mixture warmed to 20° C. and stirred for 16 h under $N_2$. The yellow mixture is poured into a brine solution (500 mL) and extracted with EtOAc (4×200 mL). The organic layers are re-combined and dried over anhydrous sodium sulfate, filtered and the solvent evaporated. The residue is purified via flash silica gel chromatography (330 g, 0-100% EtOAc in petroleum ether) to give (2Z)-2-(dimethylaminomethylene)-3-methyl-cyclopentanone as a yellow oil (34 g, 199.7 mmol, 82%). ES/MS (m/z): 154.2 (M+H).

Step B: (2Z)-2-(dimethylaminomethylene)-3-methyl-cyclopentanone (13.46 g, 87.85 mmol) is dissolved in MeOH (100 mL). To this mixture piperidine (7.5 g, 88 mmol) is added followed by methyl cyanoacetate (17.6 g, 176 mmol). The mixture is heated to 80° C. under $N_2$ for 18 h. After this time, volatile organics are evaporated under reduced pressure and the residue purified via silica gel chromatography (120 g, 0-60% EtOAc in petroleum ether) to give methyl 5-methyl-2-oxo-1,5,6,7-tetrahydrocyclopenta[b]pyridine-3-carboxylate as a brown solid (14 g, 60.8 mmol, 69%). $^1$H NMR (400.15 MHz, CDCl$_3$): 7.96 (s, 1H), 7.21 (s, 1H), 3.86 (s, 3H), 3.12-3.03 (m, 1H), 2.92-2.82 (m, 2H), 2.35-2.28 (m, 1H), 1.64-1.55 (m, 1H), 1.19 (d, J=6.9 Hz, 3H).

Step C: Methyl 5-methyl-2-oxo-1,5,6,7-tetrahydrocyclopenta[b]pyridine-3-carboxylate (3.2 g, 15 mmol) is dissolved in acetone (200 mL). To this solution, potassium carbonate (4.2 g, 30 mmol) is added followed by iodomethane (8.6 g. 61 mmol). The mixture is stirred at 20° C. for 12 h. After this time, the reaction is quenched by adding an aqueous saturated solution of ammonium chloride (100 mL), then the mixture extracted with EtOAc (2×200 mL), the organic layers combined, and dried over anhydrous sodium sulfate, filtered, and the solvent evaporated. The residue is purified via flash silica gel chromatography (120 g, 0-80% EtOAc in petroleum ether) to give methyl 1,5-dimethyl-2-oxo-6,7-dihydro-5H-cyclopenta[b]pyridine-3-carboxylate as a yellow oil (2.82 g, 12.7 mmol, 84%). ES/MS (m/z): 222.3 (M+H).

Step D: Preparation 1: Methyl 1,5-dimethyl-2-oxo-6,7-dihydro-5H-cyclopenta[b]pyridine-3-carboxylate (4.48 g, 20.2 mmol) is dissolved in THF (50 mL) and water (50 mL). To this solution, lithium hydroxide (5.78 g, 229 mmol) is added, and stirred at 40° C. for 2 h. After this time, the mixture is cooled to RT and diluted with water (30 mL), and then brought to pH ~4 with 1M aqueous HCl solution. The mixture is extracted with EtOAc (3×300 mL), the organic layers combined and dried over anhydrous sodium sulfate, then filtered and the solvent evaporated to give the title product as a yellow solid (4.1 g, 20 mmol, 98%). $^1$H NMR (400.14 MHz, d6-DMSO): 14.93 (s, 1H), 8.26 (s, 1H), 3.59 (s, 3H), 3.22-3.10 (m, 3H), 2.41-2.32 (m, 1H), 1.69-1.63 (m, 1H), 1.23 (d, J=6.9 Hz, 3H).

Preparation 2

(5R)-4-Hydroxy-1,5-dimethyl-2-oxo-6,7-dihydro-5H-cyclopenta[b]pyridine-3-carboxylic acid

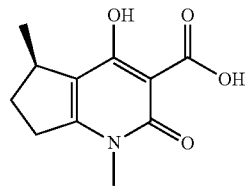 [SMILES: C[C@@H]1CCc2c1c(O)c(C(=O)O)c(=O)n2C]

Step A: (5R)-2-isopropylidene-5-methyl-cyclohexanone (95 g, 511.7 mmol) is stirred in DCM (400 mL). Formylperoxysodium (26.2 g, 312 mmol) is added and cooled to −10° C. Bromine (38.37 mL, 747 mmol) is added dropwise over 40 min, and after complete addition, stirring is continued at −10° C. for 1 h. The mixture is filtered, and the filtrate cooled to −40° C. Ethoxy sodium (20% solution by mass in EtOH, 450 mL) is added to the solution and the reaction stirred at −40° C. for 1 h., then warmed to RT and stirred an additional 16 h. The mixture is quenched with 1N aqueous HCl solution (300 mL) and extracted with EtOAc (500 mL×2). The organic layers are combined and washed with brine (300 mL) then dried over anhydrous sodium sulfate, filtered, and concentrated under vacuum. The mixture is purified via silica gel chromatography (200 g, 5% EtOAc in heptane) to give ethyl (5R)-2-isopropylidene-5-methyl-cyclopentanecarboxylate as a yellow oil (60 g, 306.7 mmol, 60%). ES/MS (m/z): 197.0 (M+H).

Step B: Ethyl (5R)-2-isopropylidene-5-methyl-cyclopentanecarboxylate (25 g, 127.4 mmol) is dissolved in 5% aqueous acetone (500 mL) and cooled to 0° C. Ozone is sparged through the solution for 12 h maintaining the temperature below 5° C. The mixture is purged with argon for 30 min then diluted with water (400 mL) and extracted with DCM (300 mL×2). The organics are combined and washed with brine (300 mL) then dried over anhydrous sodium sulfate, filtered, and concentrated under vacuum to give ethyl (2R)-2-methyl-5-oxo-cyclopentanecarboxylate as a colorless syrup (20.1 g, 70.8 mmol, 56%). ES/MS (m/z): 171.9 (M+H).

Step C: Ethyl (2R)-2-methyl-5-oxo-cyclopentanecarboxylate (10 g, 58.8 mmol) is dissolved in THF (50 mL). Methanamine (2M in THF, 176 mL, 352 mmol) is added and stirred at RT for 24 h, then concentrated under vacuum. The residue is diluted with water (100 mL) and then extracted with EtOAc (150 mL×2). The organic layers are combined, dried over anhydrous sodium sulfate, filtered, and concentrated under vacuum. ES/MS (m/z): 184.05 (M+H). The residue is dissolved in toluene (100 mL) and the mixture cooled to 0° C. 3-Chloro-3-oxo-propanoate (6.2 g, 41.2 mmol), and sodium acetate (6.8 g, 81 mmol) are added, and the mixture stirred at RT for 16 h, then diluted with water (100 mL) and extracted with EtOAc (150 mL×2). The organic layers are combined and washed with brine (100 mL), dried over anhydrous sodium sulfate, filtered, and evaporated under vacuum to give ethyl (5R)-2-[(3-ethoxy-3-oxo-propanoyl)-methyl-amino]-5-methyl-cyclopentene-1-carboxylate (8.6 g, 17.4 mmol, 25%). ES/MS (m/z): 298.0 (M+H).

Step D: Ethyl (5R)-2-[(3-ethoxy-3-oxo-propanoyl)-methyl-amino]-5-methyl-cyclopentene-1-carboxylate (17.2 g, 57.8 mmol) is dissolved in EtOH (180 mL) and ethoxy sodium (29.5 g, 86.7 mmol) is added, and stirred at RT for 2 h. The mixture is concentrated under vacuum, and 1N aqueous HCl solution (100 mL) added, then extracted with DCM (200 mL×2). The organic layers are combined, washed with brine (100 mL), dried over anhydrous sodium sulfate, filtered, and evaporated to give ethyl (5R)-4-hydroxy-1,5-dimethyl-2-oxo-6,7-dihydro-5H-cyclopenta[b]pyridine-3-carboxylate as a brown solid (11 g, 36.8 mmol, 64%). ES/MS (m/z): 251.9 (M+). Chiral method: Column: Chiral Pak IG (250×4.6 mm×5 um) mobile phase A: 0.1% DEA n n-hexane mobile, phase B: DCM/MeOH (50/50). A/B=80/20 @ 1.0 mL/min. Retention time=9.137 min.

Step E; Preparation 2: Ethyl (5R)-4-hydroxy-1,5-dimethyl-2-oxo-6,7-dihydro-5H-cyclopenta[b]pyridine-3-carboxylate (300 mg, 1.19 mmol) is diluted with 3N aqueous HCl solution (10 mL) and stirred at 65° C. for 24 h. The mixture is diluted with water (50 mL) and extracted with EtOAc (30 mL×2). The organics layers are combined, washed with brine (30 mL), dried over anhydrous sodium sulfate, filtered, and evaporated under vacuum to give the title product as a white solid (110 mg, 492 mmol, 62%). ES/MS (m/z): 223.8 (M+).

Alternative Preparation 2

(5R)-4-Hydroxy-1,5-dimethyl-2-oxo-6,7-dihydro-5H-cyclopenta[b]pyridine-3-carboxylic acid

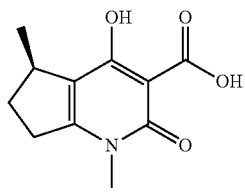 [SMILES: C[C@@H]1CCc2c1c(O)c(C(=O)O)c(=O)n2C]

Step A: (5R)-2-isopropylidene-5-methyl-cyclohexanone (95 g, 511.7 mmol) is stirred in DCM (400 mL). Sodium bicarbonate (26.2 g, 312 mmol) is added and cooled to −10° C. Bromine (38.37 mL, 747 mmol) is added dropwise over 40 min, and after complete addition, stirring is continued at −10° C. for 1 h. The mixture is filtered, and the filtrate cooled to −40° C. Ethoxy sodium (20% solution by mass in EtOH, 450 mL) is added to the solution and the reaction stirred at −40° C. for 1 h., then warmed to RT and stirred an additional 16 h. The mixture is quenched with 1N aqueous HCl solution (300 mL) and extracted with EtOAc (500 mL×2). The organic layers are combined and washed with brine (300 mL) then dried over anhydrous sodium sulfate, filtered, and concentrated under vacuum. The mixture is purified via silica gel chromatography (200 g. 5% EtOAc in heptane) to give ethyl (5R)-2-isopropylidene-5-methyl-cyclopentanecarboxylate as a yellow oil (60 g, 306.7 mmol, 60%). ES/MS (m/z): 197.0 (M+H).

Step B: Ethyl (5R)-2-isopropylidene-5-methyl-cyclopentanecarboxylate (25 g, 127.4 mmol) is dissolved in 5% aqueous acetone (500 mL) and cooled to 0° C. Ozone is sparged through the solution for 12 h maintaining the temperature below 5° C. The mixture is purged with argon for 30 min then diluted with water (400 mL) and extracted with DCM (300 mL×2). The organics are combined and washed with brine (300 mL) then dried over anhydrous sodium sulfate, filtered, and concentrated under vacuum to give ethyl (2R)-2-methyl-5-oxo-cyclopentanecarboxylate as a colorless syrup carried forward without purification (20.1 g, 70.8 mmol, 56%).

Step C: Ethyl (2R)-2-methyl-5-oxo-cyclopentanecarboxylate (10 g, 58.8 mmol) is dissolved in THF (50 mL). Methanamine (2M in THF, 176 mL, 352 mmol) is added and stirred at RT for 24 h, then concentrated under vacuum. The residue is diluted with water (100 mL) and then extracted with EtOAc (150 mL×2). The organic layers are combined, dried over anhydrous sodium sulfate, filtered, and concentrated under vacuum. ES/MS (m/z): 184.05 (M+H). The residue is dissolved in toluene (100 mL) and the mixture cooled to 0° C. Ethyl-3-chloro-3-oxo-propanoate (6.2 g, 41.2 mmol), and sodium acetate (6.8 g, 81 mmol) are added, and the mixture stirred at RT for 16 h, then diluted with water (100 mL) and extracted with EtOAc (150 mL×2). The organic layers are combined and washed with brine (100 mL), dried over anhydrous sodium sulfate, filtered, and evaporated under vacuum to give ethyl (5R)-2-[(3-ethoxy-3-oxo-propanoyl)-methyl-amino]-5-methyl-cyclopentene-1-carboxylate (8.6 g, 17.4 mmol, 25%). ES/MS (m/z): 298.0 (M+H).

Step D: Ethyl (5R)-2-[(3-ethoxy-3-oxo-propanoyl)-methyl-amino]-5-methyl-cyclopentene-1-carboxylate (17.2 g, 57.8 mmol) is dissolved in EtOH (180 mL) and ethoxy sodium (29.5 g, 86.7 mmol) is added, and stirred at RT for 2 h. The mixture is concentrated under vacuum, and 1N aqueous HCl solution (100 mL) added, then extracted with DCM (200 mL×2). The organic layers are combined, washed with brine (100 mL), dried over anhydrous sodium sulfate, filtered, and evaporated to give ethyl (5R)-4-hydroxy-1,5-dimethyl-2-oxo-6,7-dihydro-5H-cyclopenta[b]pyridine-3-carboxylate as a brown solid (11 g, 36.8 mmol, 64%). ES/MS (m/z): 251.9 (M+H). Chiral method: Column: Chiral Pak IG (250×4.6 mm×5 um) mobile phase A: 0.1% DEA in n-hexane mobile, phase B: DCM/MeOH (50/50). A/B=80/20 @ 1.0 mL/min. Retention time=9.137 min.

Step E: Preparation 2: Ethyl (5R)-4-hydroxy-1,5-dimethyl-2-oxo-6,7-dihydro-5H-cyclopenta[b]pyridine-3-carboxylate (300 mg, 1.19 mmol) is diluted with 3N aqueous HCl solution (10 mL) and stirred at 65° C. for 24 h. The mixture is diluted with water (50 mL) and extracted with EtOAc (30 mL×2). The organic layers are combined, washed with brine (30 mL), dried over anhydrous sodium sulfate, filtered, and evaporated under vacuum to give the title product as a white solid (110 mg, 492 mmol, 62%). ES/MS (m/z): 223.8 (M+H).

Preparation 3

Ethyl (5S)-4-hydroxy-1,5-dimethyl-2-oxo-6,7-dihydro-5H-cyclopenta[b]pyridine-3-carboxylate

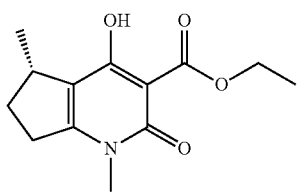 [SMILES: CCOC(=O)c1c(O)c2c(n(C)c1=O)CC[C@@H]2C]

Step A: Diatomaceous earth (100 g) is stirred in DCM (1.25 L) and pyridinium chlorochromate (202 g, 918 mmol) added at RT. To this orange suspension, (3S)-3,7-dimethyl-oct-6-en-1-ol (50 g, 304 mmol) is added dropwise over 15 min, and stirring continued for 36 h. The reaction is filtered through celite and wash bed with MTBE (1 L). The filtrate is washed with 1N aqueous HCl (500 mL×2) and saturated aqueous sodium bicarbonate solution (300 mL), then organics dried over anhydrous sodium sulfate, filtered, and evaporated under vacuum to give (5S)-2-isopropenyl-5-methyl-cyclohexanone as a brown oil (43 g, 282 mmol, 84%). ES/MS (m/z): 152.9 (M+).

Step B: (5S)-2-Isopropenyl-5-methyl-cyclohexanone (43 g, 282 mmol) is dissolved in EtOH (300 mL). Sodium hydroxide (5.64 g, 141 mmol) is added and heated to 80° C. for 24 h. The solvent is evaporated to give (5S)-2-isopropylidene-5-methyl-cyclohexanone as a brown oil (20 g, 131 mmol, 47%). ES/MS (m/z): 152.9 (M+).

Step C; Preparation 3: Starting from (5S)-2-isopropylidene-5-methyl-cyclohexanone, ethyl (5S)-4-hydroxy-1,5-dimethyl-2-oxo-6,7-dihydro-5H-cyclopenta[b]pyridine-3-carboxylate is prepared in a manner essentially analogous to the method of Preparation 2 using the appropriate reagents and adjusting the reaction time to determine completion of the reaction. ES/MS (m/z): 252.1 (M+H). Chiral method: Column: Chiral Pak IG (250×4.6 mm×5 um), mobile phase A: 0.1% DEA in n-hexane, mobile phase B: DCM/MeOH (50/50). A/B=80/20 @ 1.0 mL/min. Retention time=9.942 min.

Preparation 4

(5R)-1,5-Dimethyl-2-oxo-6,7-dihydro-5H-cyclopenta[b]pyridine-3-carboxylic acid

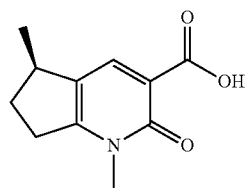

Step A: Ethyl (5R)-4-hydroxy-1,5-dimethyl-2-oxo-6,7-dihydro-5H-cyclopenta[b]pyridine-3-carboxylate (2.4 g, 9.6 mmol) (from Preparation 2, step D) is dissolved in DCM (50 mL) and cooled to 0° C. under $N_2$. Triethylamine (4 mL, 28.7 mmol) is added followed by trifluoromethylsulfonyl trifluoromethanesulfonate (2.4 mL, 14 mmol) and stirred for 2 h. After this time the mixture is poured into ice water (20 mL) and extracted with DCM (200 mL×2). The organic layers are combined, and dried over anhydrous sodium sulfate, filtered, and evaporated under vacuum to give ethyl (5R)-1,5-dimethyl-2-oxo-4-(trifluoromethylsulfonyloxy)-6,7-dihydro-5H-cyclopenta[b]pyridine-3-carboxylate as a dark brown syrup (3.6 g, 9.4 mmol, 98%). ES/MS (m/z): 384.0 (M+H).

Step B: Ethyl (5R)-1,5-dimethyl-2-oxo-4-(trifluoromethylsulfonyloxy)-6,7-dihydro-5H-cyclopenta[b]pyridine-3-carboxylate (3.5 g, 9.1 mmol) is dissolved DMF (50 mL) under $N_2$. Triethylsilane (1.2 g, 10 mmol), N,N-diethyleneamine (4 mL, 28 mmol), and dichloropalladium triphenylphosphine (640 mg, 0.91 mmol) are added and the mixture heated to 80° C. for 4 h. The mixture is diluted with water (400 mL) and then extracted with EtOAc (200 mL×2). The organic layers are combined, washed with brine (100 mL), dried over anhydrous sodium sulfate, filtered, and then the volatiles evaporated under vacuum. The residue is purified via silica gel chromatography (120 g, 5% MeOH in DCM) to give ethyl (5R)-1,5-dimethyl-2-oxo-6,7-dihydro-5H-cyclopenta[b]pyridine-3-carboxylate (800 mg, 3.4 mmol, 37%). ES/MS (m/z): 236.0 (M+H). Chiral method: Column: Chiral Pak IC (150×4.6 mm×3 um), mobile phase A: 0.1% DEA n n-hexane, mobile phase B: DCM/MeOH (50/50). A/B=70/30 @ 0.7 mL/min. Retention time=11.937 min.

Step C: Preparation 4: Ethyl (5R)-1,5-dimethyl-2-oxo-6,7-dihydro-5H-cyclopenta[b]pyridine-3-carboxylate (100 mg, 0.425 mmol) is dissolved in THF (1 mL) and water (1 mL) and lithium hydroxide (36 mg, 0.841 mmol) added, and stirred for 16 h. The mixture is diluted with water (40 mL) and washed with DCM (20 mL×2). The aqueous layer is acidified with 1N aqueous HCl solution (3 mL) and extracted with DCM (30 mL×2). The organic layers are combined, and dried over sodium sulfate, filtered, and evaporated under vacuum to give the title product as a brown solid (60 mg, 0.289 mmol, 68%). ES/MS (m/z): 207.9 (M+).

Alternatively, this product can also be prepared by separation of methyl 1,5-dimethyl-2-oxo-6,7-dihydro-5H-cyclopenta[b]pyridine-3-carboxylate (from preparation 1) via chiral SFC chromatography (0.1% $NH_4OH$-IPA; Column: DAICEL CHIRALPAK® AS (250 mm×30 mm, 10 um); Begin B: 20%; End B: 20%; Flow Rate: 60 mL/min), and treating isomer 2 with analogous procedure as preparation 1 step D using the appropriate reagents and adjusting the reaction time to determine completion of the reaction.

Alternative Preparation 4

(5R)-1,5-Dimethyl-2-oxo-6,7-dihydro-5H-cyclopenta[b]pyridine-3-carboxylic acid

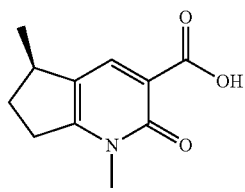

Step A: Ethyl (5R)-4-hydroxy-1,5-dimethyl-2-oxo-6,7-dihydro-5H-cyclopenta[b]pyridine-3-carboxylate (2.4 g, 9.6 mmol) (from Preparation 2, step D) is dissolved in DCM (50 mL) and cooled to 0° C. under N₂. Triethylamine (4 mL, 28.7 mmol) is added followed by trifluoromethylsulfonyl trifluoromethanesulfonate (2.4 mL, 14 mmol) and stirred for 2 h. After this time the mixture is poured into ice water (20 mL) and extracted with DCM (200 mL×2). The organic layers are combined, and dried over anhydrous sodium sulfate, filtered, and evaporated under vacuum to give ethyl (5R)-1,5-dimethyl-2-oxo-4-(trifluoromethylsulfonyloxy)-6,7-dihydro-5H-cyclopenta[b]pyridine-3-carboxylate as a dark brown syrup (3.6 g, 9.4 mmol, 98%). ES/MS (m/z): 384.0 (M+H).

Step B: Ethyl (5R)-1,5-dimethyl-2-oxo-4-(trifluoromethylsulfonyloxy)-6,7-dihydro-5H-cyclopenta[b]pyridine-3-carboxylate (3.5 g, 9.1 mmol) is dissolved DMF (50 mL) under N₂. Triethylsilane (1.2 g, 10 mmol), triethylamine (4 mL, 28 mmol), and bis(triphenylphosphine)palladium(II) dichloride (640 mg, 0.91 mmol) are added and the mixture heated to 80° C. for 4 h. The mixture is diluted with water (400 mL) and then extracted with EtOAc (200 mL×2). The organic layers are combined, washed with brine (100 mL), dried over anhydrous sodium sulfate, filtered, and then the volatiles evaporated under vacuum. The residue is purified via silica gel chromatography (120 g, 5% MeOH in DCM) to give ethyl (5R)-1,5-dimethyl-2-oxo-6,7-dihydro-5H-cyclopenta[b]pyridine-3-carboxylate (800 mg, 3.4 mmol, 37%). ES/MS (m/z): 236.0 (M+H). Chiral method: Column: Chiral Pak IC (150×4.6 mm×3 um), mobile phase A: 0.1% DEA n n-hexane, mobile phase B: DCM/MeOH (50/50). A/B=70/30 @ 0.7 mL/min. Retention time=11.937 min.

Step C: Preparation 4: Ethyl (5R)-1,5-dimethyl-2-oxo-6,7-dihydro-5H-cyclopenta[b]pyridine-3-carboxylate (100 mg, 0.425 mmol) is dissolved in THF (1 mL) and water (1 mL) and lithium hydroxide (36 mg, 0.841 mmol) added, and stirred for 16 h. The mixture is diluted with water (40 mL) and washed with DCM (20 mL×2). The aqueous layer is acidified with 1N aqueous HCl solution (3 mL) and extracted with DCM (30 mL×2). The organic layers are combined, and dried over sodium sulfate, filtered, and evaporated under vacuum to give the title product as a brown solid (60 mg, 0.289 mmol, 68%). ES/MS (m/z): 207.9 (M+H).

Alternatively, this product can also be prepared by separation of methyl 1,5-dimethyl-2-oxo-6,7-dihydro-5H-cyclopenta[b]pyridine-3-carboxylate (from preparation 1) via chiral SFC chromatography (0.1% NH₄OH-IPA; Column: DAICEL CHIRALPAK® AS (250 mm×30 mm, 10 um); Begin B: 20%; End B: 20%; Flow Rate: 60 mL/min), and treating isomer 2 with analogous procedure as preparation 1 step D using the appropriate reagents and adjusting the reaction time to determine completion of the reaction.

Preparation 5

(5S)-1,5-Dimethyl-2-oxo-6,7-dihydro-5H-cyclopenta[b]pyridine-3-carboxylic acid

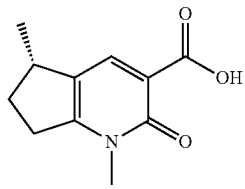

Starting from ethyl (5S)-4-hydroxy-1,5-dimethyl-2-oxo-6,7-dihydro-5H-cyclopenta[b]pyridine-3-carboxylate this compound is prepared in a manner essentially analogous to the method of Preparation 4 using the appropriate reagents and adjusting the reaction time to determine completion of the reaction. ES/MS (m/z): 207.8 (M+). ¹H NMR (400.13 MHz, d6-DMSO): 1.23 (d, J=6.9 Hz, 3H), 1.69-1.63 (m, 1H), 2.41-2.32 (m, 1H), 3.21-3.10 (m, 3H), 3.59 (s, 3H), 8.25 (s, 1H).

Alternatively, this product can also be prepared by separation of methyl 1,5-dimethyl-2-oxo-6,7-dihydro-5H-cyclopenta[b]pyridine-3-carboxylate (from preparation 1) via chiral SFC chromatography (0.1% NH₄OH-IPA; column: DAICEL CHIRALPAK® AS (250 mm×30 mm, 10 um); begin B: 20%; end B: 20%; flow rate: 60 mL/min.), and treating isomer 1 with analogous procedure as preparation 1 step D using the appropriate reagents and adjusting the reaction time to determine completion of the reaction.

Preparation 6

4-Hydroxy-1,5-dimethyl-2-oxo-6,7-dihydro-5H-cyclopenta[b]pyridine-3-carboxylic acid and 4-Hydroxy-1,6-dimethyl-2-oxo-6,7-dihydro-5H-cyclopenta[b]pyridine-3-carboxylic acid

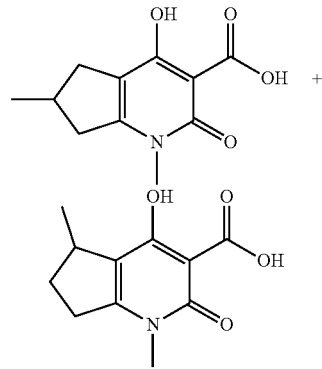

Step A: 3-Methylhexanedioic acid (5 g, 31.2 mmol) is dissolved in sulfuric acid (1.1 g, 11 mmol) and MeOH (62 mL). The mixture is stirred at 68° C. for 15 h, concentrated under vacuum, diluted with EtOAc (200 mL) and washed with water (100 mL×2). The organic layer is dried over anhydrous magnesium sulfate, filtered, and evaporated under vacuum to give dimethyl 3-methylhexanedioate as a light-yellow liquid (5.2 g, 28 mmol, 89%). ¹H NMR (400.14 MHz, d6-DMSO): 3.34 (s, 6H), 3.24-3.12 (m, 3H), 2.40-2.33 (m, 2H), 1.69-1.65 (m, 2H), 1.23 (d, J=6.8 Hz, 3H).

Step B: Dimethyl 3-methylhexanedioate (36.94 g, 157 mmol) is dissolved in toluene (300 mL). Potassium t-butoxide (37.2 g, 315 mmol) is added and stirred at RT for 12 h. The mixture is poured into EtOAc (500 mL) and 1N aqueous HCl (500 mL). The organic layers are separated and dried over anhydrous magnesium sulfate, filtered, and evaporated under vacuum. The residue is purified via silica gel chromatography (0-80% EtOAc in petroleum ether) to give methyl 2-methyl-5-oxo-cyclopentanecarboxylate and methyl 4-methyl-2-oxo-cyclopentanecarboxylate as a mixture of regio and stereo isomers as a red liquid (19.3 g, 47.6 mmol, 30%). ES/MS (m/z): 157.0 (M+H). ¹H NMR (400.13 MHz, CDCl₃): 4.15-4.04 (m, 1H), 3.68 (t, J=5.4 Hz, 6H), 3.29-3.24 (m, 1H), 3.17 (dd, J=8.1, 12.2 Hz, 1H), 2.58-2.46 (m, 7H), 1.97 (s, 1H), 1.47-1.37 (m, 1H), 1.13-1.11 (m, 4H), 1.05-1.02 (m, 2H).

Step C: A mixture of methyl 2-methyl-5-oxo-cyclopentanecarboxylate and methyl 4-methyl-2-oxo-cyclopentanecarboxylate (13.9 g, 34.3 mmol) is dissolved in methylamine (2M solution in THF, 147 mL, 294 mmol) with 4 Å molecular sieves (5 g) and stirred at 40° C. for 48 h. The mixture is diluted with EtOAc (500 mL) and washed with water (300 mL×2). The organic layer is dried over anhydrous magnesium sulfate, filtered, and evaporated under vacuum. The residue is purified via silica gel chromatography (120 g, 11% EtOAc in petroleum ether) to give methyl 4-methyl-2-(methylamino)cyclopentene-1-carboxylate and methyl 5-methyl-2-(methylamino)cyclopentene-1-carboxylate as a mixture of regio and stereo isomers as a white solid (10.75 g, 24.8 mmol, 72%). ES/MS (m/z): 170.2 (M+H). $^1$H NMR (400.14 MHz, CDCl$_3$): 3.60 (d, J=4.0 Hz, 6H), 2.83 (dd, J=2.8, 5.3 Hz, 6H), 2.79-2.73 (m, 1H), 2.67-2.60 (m, 2H), 2.58-2.41 (m, 2H), 2.11-2.03 (m, 3H), 2.01-1.96 (m, 1H), 1.43-1.41 (m, 1H), 1.21-1.16 (m, 1H), 1.00 (dd, J=3.9, 6.8 Hz, 6H).

Step D: A mixture of methyl 4-methyl-2-(methylamino)cyclopentene-1-carboxylate and methyl 5-methyl-2-(methylamino)cyclopentene-1-carboxylate (9 g, 20 mmol) is dissolved in toluene (150 mL). Sodium acetate (8.12 g, 98 mmol) and ethyl malonyl chloride (10.9 g, 70 mmol) are added. The mixture is heated to 80° C. for 2 h. under N$_2$, then cooled to RT, diluted with EtOAc (500 mL) and washed with water (400 mL×2). The organic layer is dried over anhydrous magnesium sulfate, filtered, and concentrated under vacuum. The residue is purified via silica gel chromatography (220 g, 30% EtOAc in petroleum ether) to give methyl 2-[(3-ethoxy-3-oxo-propanoyl)-methyl-amino]-3-methyl-cyclopentene-1-carboxylate and methyl 2-[(3-ethoxy-3-oxo-propanoyl)-methyl-amino]-4-methyl-cyclopentene-1-carboxylate as a mixture of regio and stereo isomers as a white solid (14.2 g, 17.8 mmol, 86%). ES/MS (m/z): 283.9 (M+H). $^1$H NMR (400.14 MHz, CDCl$_3$): 4.16-4.04 (m, 4H), 3.66 (d, J=4.5 Hz, 3H), 3.35-3.30 (m, 3H), 2.83-2.67 (m, 4H), 2.44-2.33 (m, 2H), 2.27-2.16 (m, 4H), 1.22-1.18 (m, 6H), 1.10 (d, J=6.8 Hz, 3H), 1.04 (d, J=6.8 Hz, 3H).

Step E: A mixture of methyl 2-[(3-ethoxy-3-oxo-propanoyl)-methyl-amino]-3-methyl-cyclopentene-1-carboxylate and methyl 2-[(3-ethoxy-3-oxo-propanoyl)-methyl-amino]-4-methyl-cyclopentene-1-carboxylate (13 g, 16.4 mmol) is dissolved in ethanol (100 mL). Sodium ethoxide (1.44 g, 21.2 mmol) is added and stirred at RT for 1 h. The mixture is diluted with EtOAc (500 mL) and washed with water (300 mL×2). The organic layer is dried over anhydrous magnesium sulfate, filtered, and concentrated under vacuum. The residue is purified via silica gel chromatography (220 g, 100% EtOAc in petroleum ether) to give ethyl 4-hydroxy-1,5-dimethyl-2-oxo-6,7-dihydro-5H-cyclopenta[b]pyridine-3-carboxylate and ethyl 4-hydroxy-1,6-dimethyl-2-oxo-6,7-dihydro-5H-cyclopenta[b]pyridine-3-carboxylate as a mixture of regio and stereo isomers as a yellow solid (8.7 g, 16 mmol, 100%). ES/MS (m/z): 251.9 (M+H). $^1$H NMR (400.14 MHz, CDCl$_3$): 13.36 (d, J=16.3 Hz, 2H), 4.35 (q, J=7.1 Hz, 4H), 4.15-4.02 (m, 1H), 3.33 (d, J=3.1 Hz, 6H), 3.03 (dd, J=8.3, 17.1 Hz, 1H), 2.95-2.88 (m, 2H), 2.76 (ddd, J=17.5, 9.6, 4.9 Hz, 1H), 2.61-2.52 (m, 1H), 2.46 (dd, J=6.3, 17.1 Hz, 1H), 2.35-2.27 (m, 2H), 1.63 (ddd, J=17.8, 8.9, 4.4 Hz, 1H), 1.37 (t, J=7.1 Hz, 6H), 1.21-1.17 (m, 2H), 1.12 (d, J=6.8 Hz, 4H).

Step F: Preparation 6: A mixture of ethyl 4-hydroxy-1,5-dimethyl-2-oxo-6,7-dihydro-5H-cyclopenta[b]pyridine-3-carboxylate and ethyl 4-hydroxy-1,6-dimethyl-2-oxo-6,7-dihydro-5H-cyclopenta[b]pyridine-3-carboxylate (1 g, 1.9 mmol) is dissolved in acetic acid (10 mL). Hydrobromic acid (33% by mass in acetic acid, 9 mL) is added and the mixture heated to 80° C. for 3 h. The mixture is cooled to RT and concentrated to give the title products as a mixture of regio and stereo isomers (850 mg, 1.85 mmol, 95%). ES/MS (m/z): 224.0 (M+H). $^1$H NMR (400.13 MHz, CDCl$_3$): 15.48 (d, J=12.9 Hz, 2H), 13.55 (d, J=29.3 Hz, 2H), 3.53 (d, J=3.1 Hz, 6H), 3.47-3.43 (m, 1H), 3.22-3.15 (m, 1H), 3.10-3.03 (m, 2H), 2.97-2.89 (m, 1H), 2.77-2.63 (m, 2H), 2.51-2.42 (m, 2H), 1.90-1.89 (m, 1H), 1.31 (d, J=6.9 Hz, 2H), 1.24 (d, J=6.8 Hz, 4H).

Preparation 7

4-Hydroxy-1,5-dimethyl-2-oxo-6,7-dihydro-5H-cyclopenta[b]pyridine-3-carboxylic acid

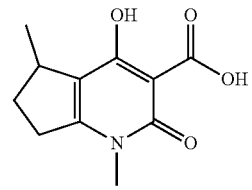 [SMILES: CC1CCc2c1c(O)c(C(=O)O)c(=O)n2C]

Step A: Methyl 2-methyl-5-oxo-cyclopentanecarboxylate (5 g, 32 mmol) is dissolved in THF (50 mL). Methylamine (2 M in THF, 96 mL, 192 mmol) is added, and stirred at RT for 6 h. Volatiles are removed under vacuum. The mixture is washed with water (100 mL) followed by brine (100 mL), dried over anhydrous sodium sulfate, filtered, and evaporated under vacuum to give methyl 5-methyl-2-(methylamino)cyclopentene-1-carboxylate as a brown syrup (5.5 g, 28 mmol, 86%). ES/MS (m/z): 170.2 (M+H).

Step B: Methyl 5-methyl-2-(methylamino)cyclopentene-1-carboxylate (5.5 g, 33 mmol) is dissolved in toluene (55 mL) under N$_2$. Sodium acetate (8 g, 97 mmol) is added, and the mixture cooled to 10° C. Ethyl 3-chloro-3-oxo-propanoate (5.3 g, 39 mmol) is added dropwise and stirred for 2 h. The mixture is diluted with EtOAc (200 mL) and water (100 mL). The organic layer is separated and washed with brine (100 mL). The organics are dried over anhydrous sodium sulfate, filtered, and evaporated under vacuum to give methyl 2-[(3-methoxy-3-oxo-propanoyl)-methyl-amino]-5-methyl-cyclopentene-1-carboxylate as a yellow oil (7.2 g, 27 mmol, 82%). ES/MS (m/z): 270.2 (M+H).

Step C: Methyl 2-[(3-methoxy-3-oxo-propanoyl)-methyl-amino]-5-methyl-cyclopentene-1-carboxylate (1 g, 2.97 mmol) is dissolved in MeOH (5 mL). Sodium methoxide (30% in MeOH, 3.6 mL) is added and stirred for 2 h. The volatiles are removed under vacuum and quenched with 1N aqueous HCl solution (20 mL). The mixture is extracted with DCM (100 mL×2). The organics are combined, washed with brine (20 mL), dried over anhydrous sodium sulfate, filtered, and evaporated to give methyl 4-hydroxy-1,5-dimethyl-2-oxo-6,7-dihydro-5H-cyclopenta[b]pyridine-3-carboxylate as a brown solid (0.55 g, 2.3 mmol, 78%). ES/MS (m/z): 238.0 (M+H).

Step D: Preparation 7: Methyl 4-hydroxy-1,5-dimethyl-2-oxo-6,7-dihydro-5H-cyclopenta[b]pyridine-3-carboxylate (3.6 g, 15 mmol) is dissolved in hydrobromic acid (5 mol/L in acetic acid, 20 mL) and stirred at 65° C. for 1 h. The mixture is concentrated under vacuum to give the title product as a yellow solid (3 g, 11 mmol, 76%). ES/MS (m/z): 224.2 (M+H).

Preparation 8

4-Hydroxy-1,5-dimethyl-2-oxo-6,7-dihydro-5H-cyclopenta[b]pyridine-3-carboxylic acid (Isomer 1) and 4-Hydroxy-1,5-dimethyl-2-oxo-6,7-dihydro-5H-cyclopenta[b]pyridine-3-carboxylic acid (Isomer 2)

Isomer 1

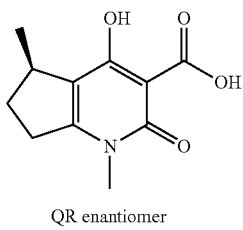

QR enantiomer

Isomer 2

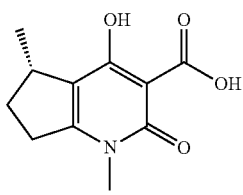

QR enantiomer

The ester from preparation 7 (step C) can be separated into enantiomers using chiral SFC chromatography. (Heptane-EtOH-0.1% NH$_4$OH, DAICEL CHIRALPAK® AY-H (250 m×30 mm, 10 μm). Then treatment of those esters in an analogous method of preparation 7 (step D) using the appropriate reagents and adjusting the reaction time to determine completion of the reaction gives the titled acid products. ES/MS (m/z): 224.2 (M+H).

Preparation 9

4-Hydroxy-1,6,6-trimethyl-2-oxo-5,7-dihydrocyclopenta[b]pyridine-3-carboxylic acid

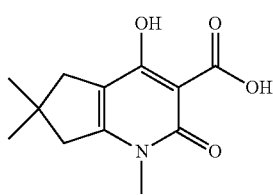 [SMILES: Cn1c2c(c(O)c(C(=O)O)c1=O)CC(C)(C)C2]

This acid is made using a method analogous to preparation 6 using the appropriate reagents and adjusting the reaction time to determine completion of the reaction. ES/MS (m/z): 238.3 (M+H).

Preparation 10

Methyl 2,2-dimethyl-5-oxo-cyclopentanecarboxylate

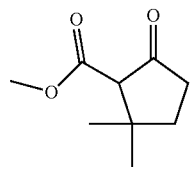

Step A: Methyl 6-methyl-3-oxo-heptanoate (2 g, 10 mmol) and N-diazo-4-methyl-benzenesulfonamide (2.8 g, 11 mmol) are dissolved in ACN (20 mL) and cooled to 0° C. Triethylamine (2.06 g, 20 mmol) is added and allowed to warm to RT overnight. The mixture is concentrated under vacuum and purified via silica gel chromatography (20 g, 100% petroleum ether) to give methyl 2-diazo-6-methyl-3-oxo-heptanoate as a yellow oil (1.2 g, 5.8 mmol, 57%) ES/MS (m/z): 199.2 (M+H). $^1$H NMR (400.14 MHz, d6-DMSO): 3.77 (s, 3H), 2.80-2.76 (m, 2H), 1.64-1.57 (m, 1H), 1.45-1.40 (m, 2H), 0.87 (d, J=6.6 Hz, 6H).

Step B: Preparation 7: Rhodium acetate (85 mg, 0.19 mmol) is dissolved in DCM (15 mL) and cooled to 0° C. under N$_2$. Methyl 2-diazo-6-methyl-3-oxo-heptanoate (1.2 g, 5.8 mmol) is added and allowed to warm to RT over 4 h. The mixture is concentrated under vacuum and purified via silica gel chromatography (20 g, 0-5% EtOAc in petroleum ether) to give methyl 2,2-dimethyl-5-oxo-cyclopentanecarboxylate as a brown oil (470 mg, 2.2 mmol, 38%). $^1$H NMR (400.14 MHz, d6-DMSO): 3.63 (s, 3H), 3.14 (s, 1H), 2.38-2.33 (m, 2H), 1.86-1.77 (m, 2H), 1.17 (s, 3H), 0.98 (s, 3H).

Preparation 11

4-Hydroxy-1,5,5-trimethyl-2-oxo-6,7-dihydrocyclopenta[b]pyridine-3-carboxylic acid

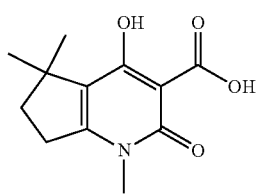 [SMILES: Cn1c2c(c(O)c(C(=O)O)c1=O)C(C)(C)CC2]

This acid is made using a method analogous to preparation 6 using the appropriate reagents and adjusting the reaction time to determine completion of the reaction. ES/MS (m/z): 238.2 (M+H).

Preparation 12

1,6,6-Trimethyl-2-oxo-7,8-dihydro-5H-quinoline-3-carboxylic acid

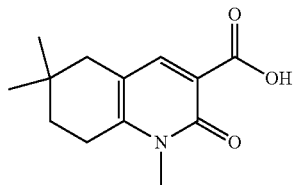 [SMILES: Cn1c2c(cc(C(=O)O)c1=O)CC(C)(C)CC2]

Step A: 4,4-Dimethylcyclohexanone (5 g, 39.6 mmol) is dissolved in methylamine (2M in THF, 160 mL, 320 mmol). Sodium sulfate (11.5 g, 79 mmol) is added and stirred in a sealed tube for 18 h. The mixture is filtered and the solid washed with DCM (10 mL). The filtrate is concentrated to give N,4,4-trimethylcyclohexanimine (6.24 g, 44.8 mmol, 113%). ES/MS (m/z): 139.2 (M+H).

Step B: N,4,4-Trimethylcyclohexanimine (220 mg, 1.58 mmol) is dissolved in MeOH (5 mL). Dimethyl methoxymethylenemalonate (370 mg, 2 mmol) is added and heated in a microwave to 150° C. for 3 h. The mixture is concentrated under vacuum and purified via silica gel chromatography (0-100% EtOAc in hexanes) to give methyl 1,6,6-trimethyl-2-oxo-7,8-dihydro-5H-quinoline-3-carboxylate (157 g, 0.63 mmol, 40%). ES/MS (m/z): 250.0 (M+H). $^1$H NMR (399.80 MHz, CDCl3): 0.99 (s, 6H), 1.63 (t, J=6.6 Hz, 2H), 2.34 (s, 2H), 2.68 (t, J=6.6 Hz, 2H), 3.55 (s, 3H), 3.89 (s, 3H), 7.88 (s, 1H).

Step C; Preparation 12: Methyl 1,6,6-trimethyl-2-oxo-7,8-dihydro-5H-quinoline-3-carboxylate (215.5 mg, 0.852 mmol) is dissolved in MeOH (10 mL). Sodium hydroxide (5M in H$_2$O, 2 mL) is added, and stirred at RT for 18 h. The mixture is quenched with 5M aqueous HCl (3 mL) and extracted with DCM (10 mL×2). The organics layers are combined, dried over anhydrous sodium sulfate, filtered, and evaporated under vacuum to give the title product (143.8 mg, 0.611 mmol, 72%). ES/MS (m/z): 235.0 (M+H).

The following compounds in Table 1 are prepared in a manner essentially analogous to the method of preparing 1,6,6-trimethyl-2-oxo-7,8-dihydro-5H-quinoline-3-carboxylic acid (Preparation 12) using the appropriate reagents and adjusting the reaction time to determine completion of the reaction.

TABLE 1

Preparations 13 to 16

| Prep No. | Chemical Name | Structure | ES/MS (m/z) (M + H) |
|---|---|---|---|
| 13 | 1-Methyl-2-oxo-7,8-dihydro-5H-pyrano[4,3-b]pyridine-3-carboxylic acid | 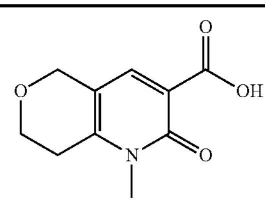 | 210.2 |
| 14 | 6-Ethyl-1-methyl-2-oxo-7,8-dihydro-5H-1,6-naphthyridine-3-carboxylic acid | 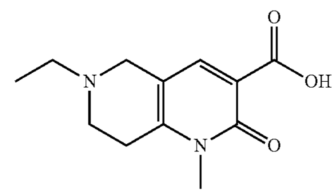 [SMILES: CCN1CCc2c(cc(C(=O)O)c(=O)n2C)C1] | 237.0 |
| 15$^a$ | 1-Methyl-2-oxo-6,7-dihydro-5H-cyclopenta[b]pyridine-3-carboxylic acid | | |
| 16 | 1-Methyl-2-oxo-6,7,8,9-tetrahydro-5H-cyclohepta[b]pyridine-3-carboxylic acid | 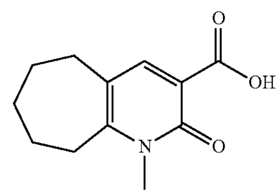 [SMILES: Cn1c2c(cc(C(=O)O)c1=O)CCCCC2] | 222.1 |

$^a$$^1$H NMR data: 1H NMR (400.16 MHz, d6-DMSO): 2.08-2.01 (m, 2H), 2.70 (t, J=7.4 Hz, 2H), 2.92 (t, J=7.5 Hz, 2H), 3.38 (s, 3H), 7.69 (s, 1H).

Preparation 17

Ethyl 4-hydroxy-1,6,6-trimethyl-2-oxo-7,8-dihydro-5H-quinoline-3-carboxylate Step A: 4,4-Dimethylcyclohexanone (5 g, 39.6 mmol) is dissolved in methylamine (2M in THF, 160 mL, 320 mmol). Sodium sulfate (11.5 g, 79 mmol) is added and stirred in a sealed tube for 18 h. The mixture is filtered and the solid washed with DCM. The filtrate is concentrated to give N,4,4-trimethylcyclohexanimine (6.24 g, 44.8 mmol, 113%). ES/MS (m/z): 139.2 (M+H).

Step B: Preparation 17: N,4,4-Trimethylcyclohexanimine (801 mg, 5.75 mmol) is dissolved in 1,2-dimethoxyethane (19 mL). Triethyl methanetricarboxylate (2.5 mL, 11.6 mmol) is added and heated in a microwave to 180° C. for 3 h. The mixture is quenched with 1N aqueous HCl solution and mixture extracted with EtOAc. The organics are combined and washed with brine, dried over anhydrous magnesium sulfate, filtered, and concentrated under vacuum. The residue is purified via silica gel chromatography (0-100%

EtOAc in hexanes) to give the title product (145 mg, 0.519 mmol, 9%). ES/MS (m/z): 280.1 (M+H).

Preparation 18

1,7,7-Trimethyl-2-oxo-5,8-dihydropyrano[4,3-b]pyridine-3-carboxylic acid

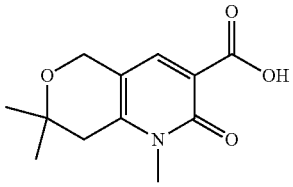 [SMILES: Cn1c2c(cc(C(=O)O)c1=O)COC(C)(C)C2]

Step A: 2,2-Dimethyltetrahydropyran-4-one (5 g, 39 mmol) is dissolved in DMF-DMA (4.9 g, 39 mmol) and heated to 100° C. for 2 h. The mixture is diluted with EtOAc (50 mL) and washed with water (50 mL×2). The organics are dried over anhydrous magnesium sulfate, filtered, evaporated under vacuum, and purified via silica gel chromatography (40 g, 0-100% EtOAc in petroleum ether) to give (5Z)-5-(dimethylaminomethylene)-2,2-dimethyl-tetrahydropyran-4-one as a yellow solid (2.49 g, 13.6 mmol, 35%). $^1$H NMR (400 MHz, $CDCl_3$) δ=7.58-7.44 (m, 1H), 4.90-4.73 (m, 2H), 3.08 (s, 6H), 2.35 (s, 2H), 1.30 (s, 6H).

Step B: (5Z)-5-(Dimethylaminomethylene)-2,2-dimethyl-tetrahydropyran-4-one (2.49 g, 13.6 mmol) is dissolved in MeOH (50 mL). Piperidine (1.16 g, 13.6 mmol) and methyl cyanoacetate (2 g, 20.4 mmol) are added and heated via microwave to 100° C. for 1 h. The mixture is concentrated and purified via silica gel chromatography (20 g, 0-10% MeOH in EtOAc) to give methyl 7,7-dimethyl-2-oxo-5,8-dihydro-1H-pyrano[4,3-b]pyridine-3-carboxylate as a red solid (1.6 g, 6.54 mmol, 48%). $^1$H NMR (400 MHz, $CDCl_3$) δ=8.06-7.96 (m, 1H), 4.63 (s, 2H), 3.92 (s, 3H), 2.78 (s, 2H), 1.33 (s, 6H).

Step C: Methyl 7,7-dimethyl-2-oxo-5,8-dihydro-1H-pyrano[4,3-b]pyridine-3-carboxylate (1.61 g, 6.79 mmol) is dissolved in acetone (20 mL). Potassium carbonate (1.9 g, 14 mmol) and iodomethane (3 g, 21 mmol) are added and stirred for 12 h. The mixture is diluted with EtOAc (50 mL) and washed with water (30 mL×2). The organics are dried over anhydrous magnesium sulfate, filtered, and evaporated under vacuum. The residue is purified via silica gel chromatography (20 g, 0-100% EtOAc in petroleum ether) to give methyl 1,7,7-trimethyl-2-oxo-5,8-dihydropyrano[4,3-b]pyridine-3-carboxylate as a red solid (985 mg, 3.9 mmol, 58%). ES/MS (m/z): 252 (M+H). $^1$H NMR (400 MHz, $CDCl_3$) δ=7.88 (s, 1H), 4.58 (s, 2H), 3.91 (s, 3H), 3.52 (s, 3H), 2.59 (s, 2H), 1.34 (s, 6H).

Step D: Preparation 18: Methyl 1,7,7-trimethyl-2-oxo-5,8-dihydropyrano[4,3-b]pyridine-3-carboxylate (909 mg, 3.6 mmol) is dissolved in THF (3 mL) and water (3 mL). Lithium hydroxide (913 mg, 36 mmol) is added and stirred at 40° C. for 2 h. The mixture is diluted with water (10 mL) and acidified with 1M aqueous HCl solution, then extracted with EtOAc (10 mL×3). The organics are combined, dried over anhydrous sodium sulfate, filtered, and concentrated under vacuum to give the title product as a yellow solid (680 mg, 2.86 mmol, 79%). ES/MS (m/z): 238 (M+H). $^1$H NMR (400 MHz, $CDCl_3$) δ=14.57-14.25 (m, 1H), 8.20-8.09 (m, 1H), 4.63-4.52 (m, 2H), 3.55 (s, 3H), 2.64-2.50 (m, 2H), 1.29 (s, 6H).

The following compounds in Table 2 are prepared in a manner essentially analogous to the method described for 1,7,7-trimethyl-2-oxo-5,8-dihydropyrano[4,3-b]pyridine-3-carboxylic acid (Preparation 18) using the appropriate reagents and adjusting the reaction time to determine completion of the reaction.

TABLE 2

Preparations 19 to 21

| Prep No. | Chemical Name | Structure | ES/MS (m/z) (M + H) |
|---|---|---|---|
| 19 | 1,7-Dimethyl-2-oxo-6,7-dihydro-5H-cyclopenta[b]pyridine-3-carboxylic acid | 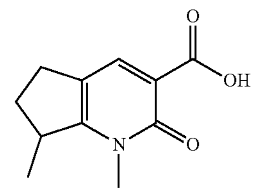 | 208.2 |
| 20 | 1,5-Dimethyl-2-oxo-5,6,7,8-tetrahydroquinoline-3-carboxylic acid | 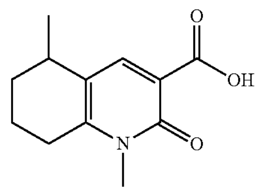 [SMILES: CC1CCCc2c1cc(C(=O)O)c(=O)n2C] | 222.3 |
| 21 | 1,6-Dimethyl-2-oxo-5,6,7,8-tetrahydroquinoline-3-carboxylic acid | 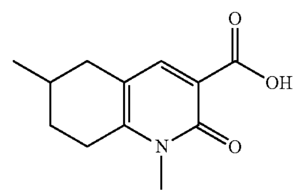 [SMILES: CC1CCc2c(cc(C(=O)O)c(=O)n2C)C1] | 222.2 |

Preparation 22

5-Isopropyl-1-methyl-2-oxo-6,7-dihydro-5H-cyclopenta[b]pyridine-3-carboxylic acid

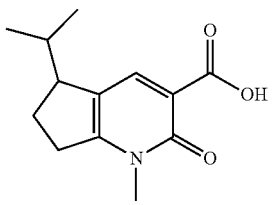 [SMILES: CC(C)C1CCc2c1cc(C(=O)O)c(=O)n2C]

Step A. Cuprous iodide (13.9 g, 73 mmol) and tributylphosphine (38 mL, 140 mmol) is stirred in THF (150 mL) for 10 min under $N_2$. The mixture is cooled to −78° C. and isopropyllithium (0.7 mol/L in pentane) (73 mL, 73 mmol) added dropwise. After complete addition, the mixture is stirred at −78° C. for 30 min under $N_2$. After this time boron trifluoride diethyl etherate (8.5 mL, 67 mmol) is added and stirred for 5 min, and cyclopent-2-en-1-one (5 g, 60.9 mmol) added. This mixture is stirred at −55° C. for 40 min under $N_2$. DMF-DMA (20 mL, 150 mmol) is then added, and the mixture warmed to 20° C. and stirred for 16 h under $N_2$. The yellow mixture is poured into a brine solution (500 mL) and extracted with EtOAc (4×200 mL). The organic layers are re-combined and dried over anhydrous sodium sulfate, filtered and the solvent evaporated. The residue is purified via flash silica gel chromatography (330 g, 0-100% EtOAc in petroleum ether) to give (2Z)-2-(dimethylaminomethylene)-3-isopropyl-cyclopentanone as a yellow oil (1.8 g, 66 mmol, 11%). ES/MS (m/z): 182.1 (M+H).

Step B: (2Z)-2-(dimethylaminomethylene)-3-isopropyl-cyclopentanone (1.7 g, 6.2 mmol) is dissolved in MeOH (30 mL). To this mixture piperidine (0.53 g, 6.19 mmol) is added followed by methyl cyanoacetate (1.2 g, 12 mmol). The mixture is heated to 80° C. under $N_2$ for 18 h. After this time, volatile organics are evaporated under reduced pressure and the residue purified via silica gel chromatography (80 g, 0-100% EtOAc in petroleum ether) to give methyl 5-isopropyl-2-oxo-1,5,6,7-tetrahydrocyclopenta[b]pyridine-3-carboxylate as a red solid (1.4 g, 5.1 mmol, 82%). ES/MS (m/z): 236.1 (M+H).

Step C: methyl 5-isopropyl-2-oxo-1,5,6,7-tetrahydrocyclopenta[b]pyridine-3-carboxylate (1 g, 3.66 mmol) is dissolved in acetone (15 mL). To this solution, potassium carbonate (770 mg, 5.52 mmol) is added followed by iodomethane (0.92 mL. 15 mmol). The mixture is stirred at 25° C. for 15 h. After this time, the reaction is quenched by adding an aqueous saturated solution of ammonium chloride (10 mL), then the mixture extracted with EtOAc (2×20 mL), the organic layers combined, and dried over anhydrous sodium sulfate, filtered, and the solvent evaporated. The residue is purified via flash silica gel chromatography (12 g, 0-100% EtOAc in petroleum ether) to give methyl 5-isopropyl-1-methyl-2-oxo-6,7-dihydro-5H-cyclopenta[b]pyridine-3-carboxylate as a red solid (0.9 g, 3.5 mmol, 97%). ES/MS (m/z): 250.1 (M+H).

Step D: Preparation 1: methyl 5-isopropyl-1-methyl-2-oxo-6,7-dihydro-5H-cyclopenta[b]pyridine-3-carboxylate (0.7 g, 2.75 mmol) is dissolved in THF (6 mL), methanol (3.5 mL), and water (1.5 mL). To this solution, lithium hydroxide (0.48 g, 11.2 mmol) is added, and stirred at 40° C. for 2 h. After this time, the mixture is cooled to RT and diluted with water (10 mL), and then brought to pH ~4 with 1M aqueous HCl solution. The mixture is extracted with EtOAc (3×30 mL), the organic layers combined and dried over anhydrous sodium sulfate, then filtered and the solvent evaporated to give the title product as a brown oil (4.1 g, 20 mmol, 98%). ES/MS (m/z): 236.1 (M+H).

Preparation 23

5-Ethyl-1-methyl-2-oxo-6,7-dihydro-5H-cyclopenta[b]pyridine-3-carboxylic acid

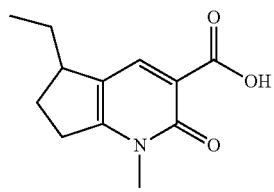 [SMILES: CCC1CCc2c1cc(C(=O)O)c(=O)n2C]

Step A: Cuprous iodide (14 g, 73.5 mmol) and tributylphosphine (38 mL, 140 mmol) is stirred in THF (150 mL) for 10 min under $N_2$. The mixture is cooled to −78° C. and ethyllithium (1.6 mol/L in ether) (46 mL, 74 mmol) added dropwise. After complete addition, the mixture is stirred at −78° C. for 30 min under $N_2$. After this time boron trifluoride diethyl etherate (8.5 mL, 67 mmol) is added and stirred for 5 min, and cyclopent-2-en-1-one (5 g, 60.9 mmol) added. This mixture is stirred at −55° C. for 40 min under $N_2$. DMF-DMA (20 mL, 150 mmol) is then added, and the mixture warmed to 20° C. and stirred for 16 h under $N_2$. The yellow mixture is poured into a brine solution (500 mL) and extracted with EtOAc (4×200 mL). The organic layers are re-combined and dried over anhydrous sodium sulfate, filtered and the solvent evaporated. The residue is purified via flash silica gel chromatography (80 g, 0-100% EtOAc in petroleum ether) to give (2Z)-2-(dimethylaminomethylene)-3-ethyl-cyclopentanone as a yellow oil (1.5 g, 63 mmol, 10%). ES/MS (m/z): 168.2 (M+H).

Step B: (2Z)-2-(dimethylaminomethylene)-3-ethyl-cyclopentanone (1 g, 4.2 mmol) is dissolved in MeOH (15 mL). To this mixture piperidine (0.5 g, 6 mmol) is added followed by methyl cyanoacetate (0.84 g, 9.4 mmol). The mixture is heated to 80° C. under $N_2$ for 18 h. After this time, volatile organics are evaporated under reduced pressure and the residue purified via silica gel chromatography (12 g, 0-100% EtOAc in petroleum ether) to give methyl 5-ethyl-2-oxo-1,5,6,7-tetrahydrocyclopenta[b]pyridine-3-carboxylate as a yellow oil (1 g, 1.8 mmol, 43%). ES/MS (m/z): 222.2 (M+H).

Step C: 5-ethyl-2-oxo-1,5,6,7-tetrahydrocyclopenta[b]pyridine-3-carboxylate (1 g, 1.8 mmol) is dissolved in acetone (10 mL). To this solution, potassium carbonate (1 g, 7.2 mmol) is added followed by iodomethane (1.2 mL. 19 mmol). The mixture is stirred at 25° C. for 16 h. After this time, the reaction is quenched by adding an aqueous saturated solution of ammonium chloride (10 mL), then the mixture extracted with EtOAc (2×20 mL), the organic layers combined, and dried over anhydrous sodium sulfate, filtered, and the solvent evaporated. The residue is purified via flash silica gel chromatography (12 g, 0-100% EtOAc in petroleum ether) to give methyl 5-ethyl-1-methyl-2-oxo-2,5,6,7-tetrahydro-1H-cyclopenta[b]pyridine-3-carboxylate as a yellow oil (0.33 g, 1.1 mmol, 60%). ES/MS (m/z): 236.1 (M+H).

Step D; Preparation 1: 5-ethyl-1-methyl-2-oxo-2,5,6,7-tetrahydro-1H-cyclopenta[b]pyridine-3-carboxylate (0.5 g, 1.4 mmol) is dissolved in THF (4 mL), methanol (2 mL), and water (1 mL). To this solution, lithium hydroxide (0.15 g, 6.2 mmol) is added, and stirred at 25° C. for 18 h. After this time, the mixture is diluted with water (50 mL), and then brought to pH ~3 with 1M aqueous HCl solution. The mixture is extracted with EtOAc (3×30 mL), the organic layers combined and dried over anhydrous sodium sulfate, then filtered and the solvent evaporated to give the title product as a yellow solid (0.36 g, 1.3 mmol, 94%). ES/MS (m/z): 222.0 (M+H).

Example 1

N-(5-Fluoropyrimidin-2-yl)-1,5-dimethyl-2-oxo-6,7-dihydro-5H-cyclopenta[b]pyridine-3-carboxamide

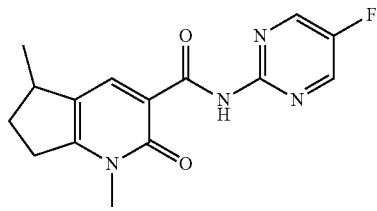

1,5-Dimethyl-2-oxo-6,7-dihydro-5H-cyclopenta[b]pyridine-3-carboxylic acid (300 mg, 1.45 mmol), 5-fluoropyrimidin-2-amine (245 mg, 2.17 mmol), and pyridine (345 mg, 4.34 mmol) are dissolved in DCM (6 mL). Phosphoryl chloride (271 mg, 1.73 mmol) is added and stirred at 25° C. for 12 h. After this time, volatiles are evaporated under reduced pressure and the residue purified via silica gel chromatography (20 g, 0-100% EtOAc in petroleum ether) to give the product as a white solid (368.3 mg, 1.21 mmol, 84%). ES/MS (m/z): 303.1 (M+H). $^1$H NMR (400.14 MHz, d6-DMSO): 12.97 (s, 1H), 8.79 (s, 2H), 8.34 (s, 1H), 3.57 (s, 3H), 3.24-3.12 (m, 3H), 2.40-2.33 (m, 1H), 1.69-1.65 (m, 1H), 1.23 (d, J=6.8 Hz, 3H).

The following compounds in Table 3 are prepared in a manner essentially analogous to the method of preparing N-(5-fluoropyrimidin-2-yl)-1,5-dimethyl-2-oxo-6,7-dihydro-5H-cyclopenta[b]pyridine-3-carboxamide (Example 1) using the appropriate reagents and adjusting the reaction time to determine completion of the reaction.

TABLE 3

Examples 2 to 14

| Ex No. | Chemical Name | Structure | ES/MS (m/z) (M + H) |
|---|---|---|---|
| 2 | N-(5-Fluoro-2-pyridyl)-1,5-dimethyl-2-oxo-6,7-dihydro-5H-cyclopenta[b]pyridine-3-carboxamide | 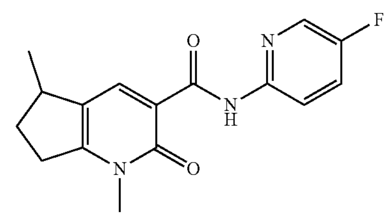 [SMILES: CC1CCc2c1cc(C(=O)Nc1ccc(F)cn1)c(=O)n2C] | 302.1 |
| 3 | N-(5-Fluorothiazol-2-yl)-1,5-dimethyl-2-oxo-6,7-dihydro-5H-cyclopenta[b]pyridine-3-carboxamide | 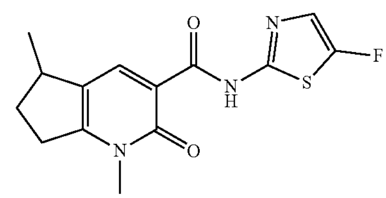 [SMILES: CC1CCc2c1cc(C(=O)Nc1ncc(F)s1)c(=O)n2C] | 308.3 |
| 4 | 1,5-Dimethyl-2-oxo-N-[5-(trifluoromethyl)-2-pyridyl]-6,7-dihydro-5H-cyclopenta[b]pyridine-3-carboxamide | 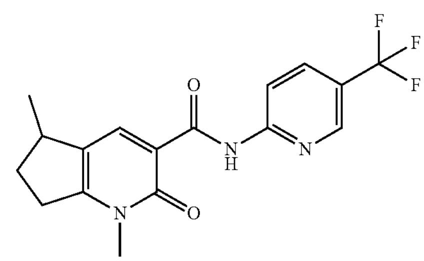 [SMILES: CC1CCc2c1cc(C(=O)Nc1ccc(C(F)(F)F)cn1)c(=O)n2C] | 352.3 |
| 5 | N-(3-Fluoro-2-pyridyl)-1,5-dimethyl-2-oxo-6,7-dihydro-5H-cyclopenta[b]pyridine-3-carboxamide | 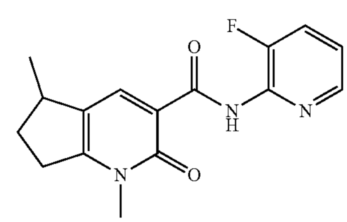 [SMILES: CC1CCc2c1cc(C(=O)Nc1ncccc1F)c(=O)n2C] | 302.3 |

TABLE 3-continued

Examples 2 to 14

| Ex No. | Chemical Name | Structure | ES/MS (m/z) (M + H) |
|---|---|---|---|
| 6 | 1,5-Dimethyl-2-oxo-N-[6-(trifluoromethyl)-3-pyridyl]-6,7-dihydro-5H-cyclopenta[b]pyridine-3-carboxamide | 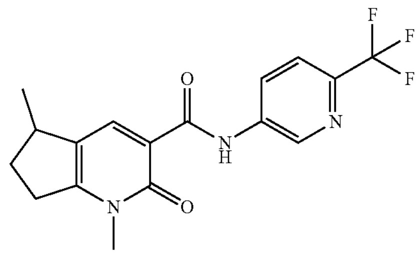 [SMILES: CC1CCc2c1cc(C(=O)Nc1ccc(C(F)(F)F)nc1)c(=O)n2C] | 352.3 |
| 7 | 1,5-Dimethyl-2-oxo-N-[4-(trifluoromethyl)pyrimidin-2-yl]-6,7-dihydro-5H-cyclopenta[b]pyridine-3-carboxamide | 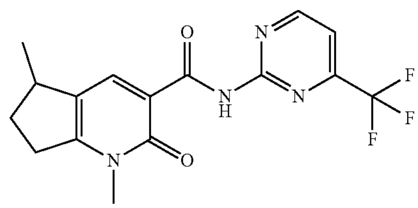 [SMILES: CC1CCc2c1cc(C(=O)Nc1nccc(C(F)(F)F)n1)c(=O)n2C] | 353.1 |
| 8 | 1,5-Dimethyl-2-oxo-N-[5-(trifluoromethyl)pyrimidin-2-yl]-6,7-dihydro-5H-cyclopenta[b]pyridine-3-carboxamide | 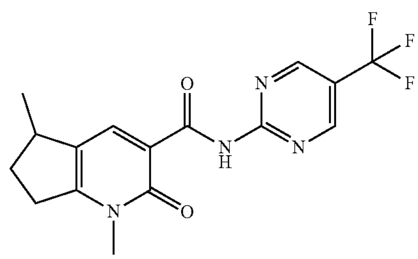 [SMILES: CC1CCc2c1cc(C(=O)Nc1ncc(C(F)(F)F)cn1)c(=O)n2C] | 353.3 |
| 9 | N-Cyclopentyl-1,5-dimethyl-2-oxo-6,7-dihydro-5H-cyclopenta[b]pyridine-3-carboxamide | 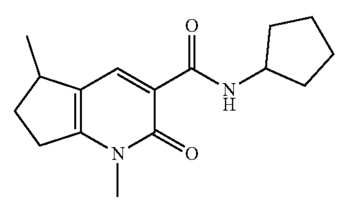 [SMILES: CC1CCc2c1cc(C(=O)NC1CCCC1)c(=O)n2C] | 275.3 |
| 10 | (5S)-1,5-Dimethyl-2-oxo-N-[5-(trifluoromethyl)-1,3,4-thiadiazol-2-yl]-6,7-dihydro-5H-cyclopenta[b]pyridine-3-carboxamide | 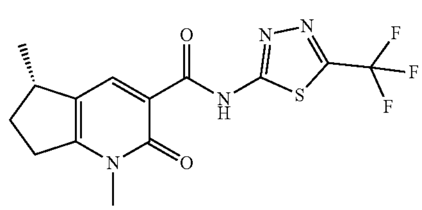 | 359.3 |
| 11 | (5S)-1,5-Dimethyl-2-oxo-N-[5-(trifluoromethyl)-1,3,4-oxadiazol-2-yl]-6,7-dihydro-5H-cyclopenta[b]pyridine-3-carboxamide | 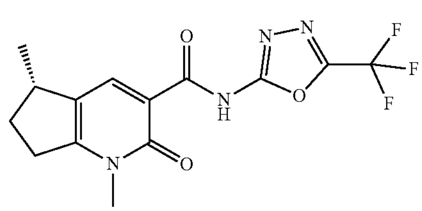 | 343.3 |

TABLE 3-continued

Examples 2 to 14

| Ex No. | Chemical Name | Structure | ES/MS (m/z) (M + H) |
|---|---|---|---|
| 12 | (5R)-N-(5-Fluoropyrimidin-2-yl)-1,5-dimethyl-2-oxo-6,7-dihydro-5H-cyclopenta[b]pyridine-3-carboxamide | 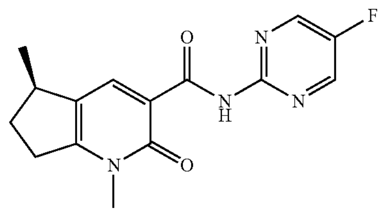 [SMILES: C[C@@H]1CCc2c1cc(C(=O)Nc1ncc(F)cn1)c(=O)n2C] | 303 |
| 13 | (5S)-N-(5-Fluoropyrimidin-2-yl)-1,5-dimethyl-2-oxo-6,7-dihydro-5H-cyclopenta[b]pyridine-3-carboxamide | 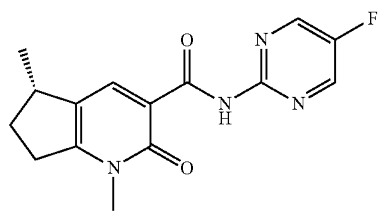 [SMILES: C[C@H]1CCc2c1cc(C(=O)Nc1ncc(F)cn1)c(=O)n2C] | 303 |
| 14 | N-(5-Fluoropyrimidin-2-yl)-1,5,5-trimethyl-2-oxo-6,7-dihydrocyclopenta[b]pyridine-3-carboxamide | 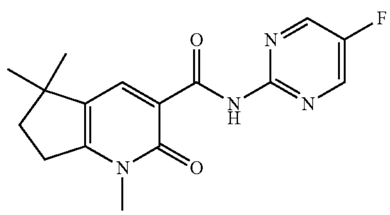 [SMILES: Cn1c2c(cc(C(=O)Nc3ncc(F)cn3)c1=O)C(C)(C)CC2] | 317.3 |

Example 15

1,5-Dimethyl-2-oxo-N-thiazol-2-yl-6,7-dihydro-5H-cyclopenta[b]pyridine-3-carboxamide

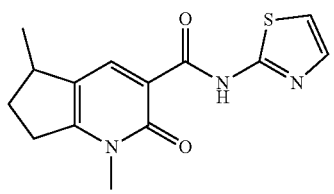 [SMILES: CC1CCc2c1cc(C(=O)Nc1nccs1)c(=O)n2C]

1,5-Dimethyl-2-oxo-6,7-dihydro-5H-cyclopenta[b]pyridine-3-carboxylic acid (500 mg, 2.4 mmol) and thiazol-2-amine (362 mg, 3.6 mmol) are dissolved in DCE (8 mL). 1-Propanephosphonic anhydride (1.7 mol/L in EtOAc) (3.07 g, 4.82 mmol) is added and the mixture heated to 80° C. for 16 h. After this time, the volatiles are evaporated under reduced pressure and residue stirred in MeOH (5 mL) for 20 min. The formed solid is filtered to obtain the title product as an off-white solid (351.39 mg, 1.18 mmol, 49%). ES/MS (m/z): 290.3 (M+H). $^1$H NMR (400.14 MHz, d6-DMSO): 13.49 (s, 1H), 8.38 (s, 1H), 7.52 (d, J=4.8 Hz, 1H), 7.28 (d, J=4.8 Hz, 1H), 3.585 (s, 3H), 3.30-2.93 (m, 3H), 2.37-2.33 (m, 1H), 1.69-1.61 (m, 1H), 1.22 (d, J=6.8 Hz, 3H).

The following compounds in Table 4 are prepared in a manner essentially analogous to the method of preparing 1,5-dimethyl-2-oxo-N-thiazol-2-yl-6,7-dihydro-5H-cyclopenta[b]pyridine-3-carboxamide (Example 15) using the appropriate reagents and adjusting the reaction time to determine completion of the reaction.

TABLE 4

Examples 16 to 53

| Ex No. | Chemical Name | Structure | ES/MS (m/z) (M + H) |
|---|---|---|---|
| 16 | (5R)-N-Isothiazol-5-yl-1,5-dimethyl-2-oxo-6,7-dihydro-5H-cyclopenta[b]pyridine-3-carboxamide | 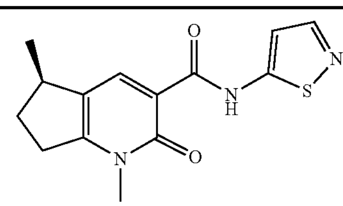 | 290.3 |

TABLE 4-continued

Examples 16 to 53

| Ex No. | Chemical Name | Structure | ES/MS (m/z) (M + H) |
|---|---|---|---|
| 17 | (5S)-N-Isothiazol-5-yl-1,5-dimethyl-2-oxo-6,7-dihydro-5H-cyclopenta[b]pyridine-3-carboxamide | 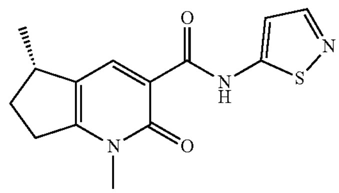 [SMILES: C[C@H]1CCc2c1cc(C(=O)Nc1ccns1)c(=O)n2C] | 290.3 |
| 18 | (5R)-N-Isothiazol-3-yl-1,5-dimethyl-2-oxo-6,7-dihydro-5H-cyclopenta[b]pyridine-3-carboxamide | 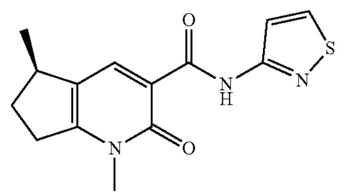 [SMILES: C[C@@H]1CCc2c1cc(C(=O)Nc1ccsn1)c(=O)n2C] | 289.9 |
| 19 | (5S)-N-Isothiazol-3-yl-1,5-dimethyl-2-oxo-6,7-dihydro-5H-cyclopenta[b]pyridine-3-carboxamide | 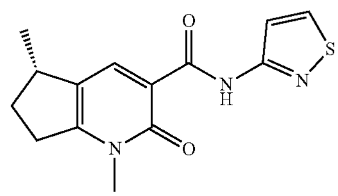 [SMILES: C[C@H]1CCc2c1cc(C(=O)Nc1ccsn1)c(=O)n2C] | 289.9 |
| 20 | (5R)-N-Isothiazol-4-yl-1,5-dimethyl-2-oxo-6,7-dihydro-5H-cyclopenta[b]pyridine-3-carboxamide | 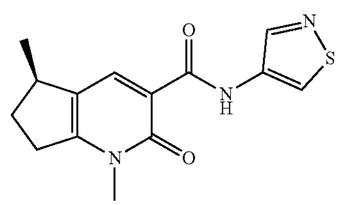 [SMILES: C[C@@H]1CCc2c1cc(C(=O)Nc1cnsc1)c(=O)n2C] | 290.3 |
| 21 | (5S)-N-Isothiazol-4-yl-1,5-dimethyl-2-oxo-6,7-dihydro-5H-cyclopenta[b]pyridine-3-carboxamide | 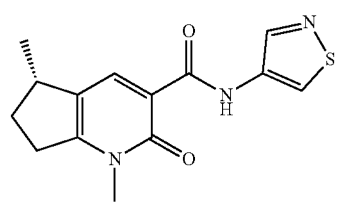 [SMILES: C[C@H]1CCc2c1cc(C(=O)Nc1cnsc1)c(=O)n2C] | 290.3 |
| 22 | (5S)-1,5-Dimethyl-2-oxo-N-(2-pyridyl)-6,7-dihydro-5H-cyclopenta[b]pyridine-3-carboxamide | 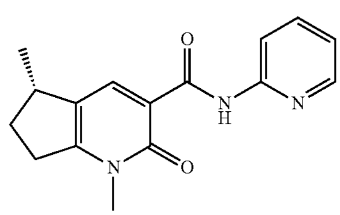 [SMILES: C[C@H]1CCc2c1cc(C(=O)Nc1ccccn1)c(=O)n2C] | 284.3 |
| 23 | (5R)-1,5-Dimethyl-2-oxo-N-(2-pyridyl)-6,7-dihydro-5H-cyclopenta[b]pyridine-3-carboxamide | 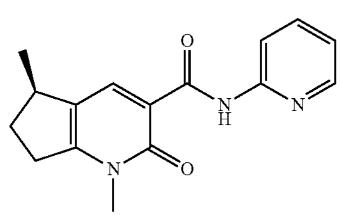 [SMILES: C[C@@H]1CCc2c1cc(C(=O)Nc1ccccn1)c(=O)n2C] | 284.3 |

TABLE 4-continued

Examples 16 to 53

| Ex No. | Chemical Name | Structure | ES/MS (m/z) (M + H) |
|---|---|---|---|
| 24 | (5S)-N-(5-Chloropyrimidin-2-yl)-1,5-dimethyl-2-oxo-6,7-dihydro-5H-cyclopenta[b]pyridine-3-carboxamide | 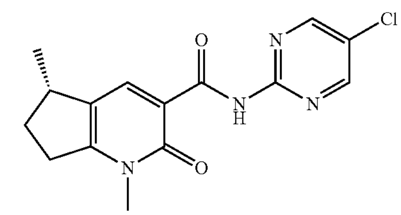 [SMILES: C[C@H]1CCc2c1cc(C(=O)Nc1ncc(Cl)cn1)c(=O)n2C] | 318.9 |
| 25 | (5R)-N-(5-Chloropyrimidin-2-yl)-1,5-dimethyl-2-oxo-6,7-dihydro-5H-cyclopenta[b]pyridine-3-carboxamide | 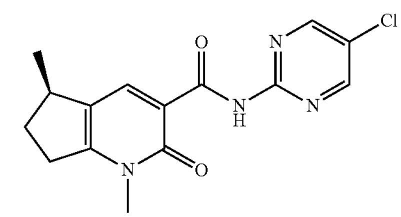 [SMILES: C[C@@H]1CCc2c1cc(C(=O)Nc1ncc(Cl)cn1)c(=O)n2C] | 318.9 |
| 26 | N-(5-Fluoro-2-pyridyl)-4-hydroxy-1,5-dimethyl-2-oxo-6,7-dihydro-5H-cyclopenta[b]pyridine-3-carboxamide | 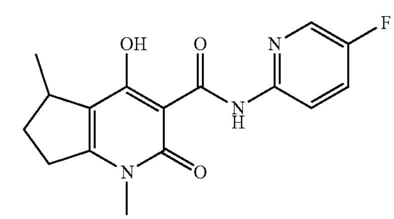 [SMILES: CC1CCc2c1c(O)c(C(=O)Nc1ccc(F)cn1)c(=O)n2C] | 318.2 |
| 27 | 4-Hydroxy-N-(5-methoxypyrimidin-2-yl)-1,5-dimethyl-2-oxo-6,7-dihydro-5H-cyclopenta[b]pyridine-3-carboxamide | 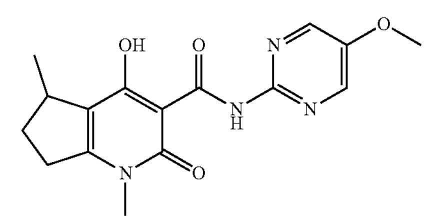 [SMILES: COc1cnc(NC(=O)c2c(O)c3c(n(C)c2=O)CCC3C)nc1] | 331.3 |
| 28 | 4-Hydroxy-1,5-dimethyl-2-oxo-N-[6-(trifluoromethyl)-3-pyridyl]-6,7-dihydro-5H-cyclopenta[b]pyridine-3-carboxamide | 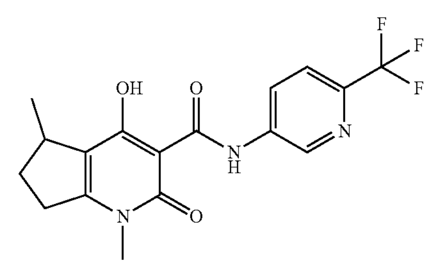 [SMILES: CC1CCc2c1c(O)c(C(=O)Nc1ccc(C(F)(F)F)nc1)c(=O)n2C] | 368.3 |
| 29 | N-(3-Fluoro-2-pyridyl)-4-hydroxy-1,5-dimethyl-2-oxo-6,7-dihydro-5H-cyclopenta[b]pyridine-3-carboxamide | 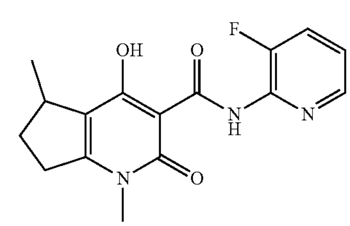 [SMILES: CC1CCc2c1c(O)c(C(=O)Nc1ncccc1F)c(=O)n2C] | 318.3 |

TABLE 4-continued

Examples 16 to 53

| Ex No. | Chemical Name | Structure | ES/MS (m/z) (M + H) |
|---|---|---|---|
| 30 | N-(5-Fluoropyrimidin-2-yl)-4-hydroxy-1,5-dimethyl-2-oxo-6,7-dihydro-5H-cyclopenta[b]pyridine-3-carboxamide | 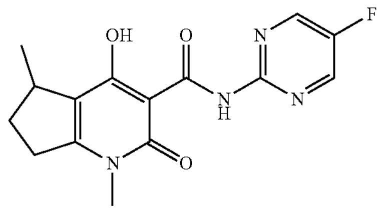 [SMILES: CC1CCc2c1c(O)c(C(=O)Nc1ncc(F)cn1)c(=O)n2C] | 319.2 |
| 31 | 4-Hydroxy-1,5-dimethyl-2-oxo-N-[4-(trifluoromethyl)pyrimidin-2-yl]-6,7-dihydro-5H-cyclopenta[b]pyridine-3-carboxamide | 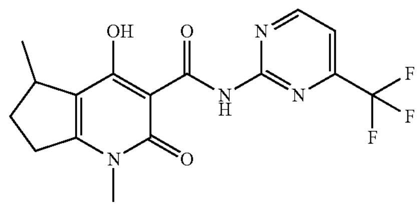 [SMILES: CC1CCc2c1c(O)c(C(=O)Nc1nccc(C(F)(F)F)n1)c(=O)n2C] | 369.3 |
| 32 | 4-Hydroxy-1,5-dimethyl-2-oxo-N-[5-(trifluoromethyl)pyrimidin-2-yl]-6,7-dihydro-5H-cyclopenta[b]pyridine-3-carboxamide | 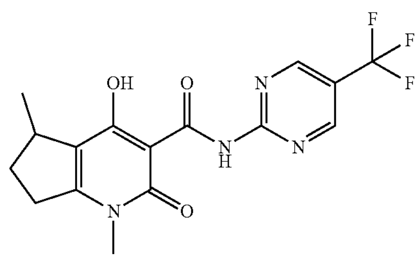 [SMILES: CC1CCc2c1c(O)c(C(=O)Nc1ncc(C(F)(F)F)cn1)c(=O)n2C] | 369.3 |
| 33 | 4-Hydroxy-1,5-dimethyl-2-oxo-N-[5-(trifluoromethyl)-2-pyridyl]-6,7-dihydro-5H-cyclopenta[b]pyridine-3-carboxamide | 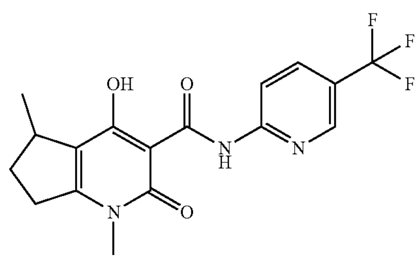 [SMILES: CC1CCc2c1c(O)c(C(=O)Nc1ccc(C(F)(F)F)cn1)c(=O)n2C] | 368.3 |
| 34 | 4-Hydroxy-1,5-dimethyl-N-oxazol-2-yl-2-oxo-6,7-dihydro-5H-cyclopenta[b]pyridine-3-carboxamide (isomer 1) | OR enantiomer | 290.3 |
| 35 | 4-Hydroxy-1,5-dimethyl-N-oxazol-2-yl-2-oxo-6,7-dihydro-5H-cyclopenta[b]pyridine-3-carboxamide (isomer 2) | OR enantiomer | 290.3 |

TABLE 4-continued

Examples 16 to 53

| Ex No. | Chemical Name | Structure | ES/MS (m/z) (M + H) |
|---|---|---|---|
| 36 | 4-Hydroxy-N-isothiazol-5-yl-1,5-dimethyl-2-oxo-6,7-dihydro-5H-cyclopenta[b]pyridine-3-carboxamide (isomer 1) | 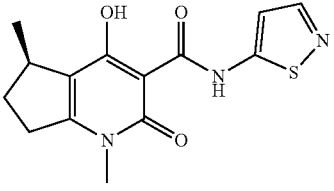 OR enantiomer | 306.3 |
| 37 | 4-Hydroxy-N-isothiazol-5-yl-1,5-dimethyl-2-oxo-6,7-dihydro-5H-cyclopenta[b]pyridine-3-carboxamide (isomer 2) | 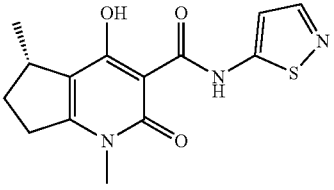 OR enantiomer | 306.3 |
| 38 | 4-Hydroxy-N-isothiazol-3-yl-1,5-dimethyl-2-oxo-6,7-dihydro-5H-cyclopenta[b]pyridine-3-carboxamide (isomer 1) | 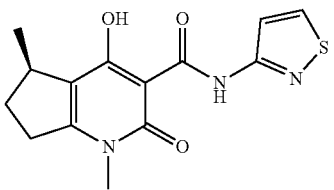 OR enantiomer | 306.3 |
| 39 | 4-Hydroxy-N-isothiazol-3-yl-1,5-dimethyl-2-oxo-6,7-dihydro-5H-cyclopenta[b]pyridine-3-carboxamide (isomer 2) | 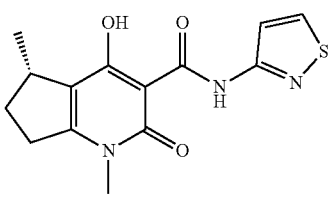 OR enantiomer | 306.3 |
| 40 | 4-Hydroxy-N-isothiazol-4-yl-1,5-dimethyl-2-oxo-6,7-dihydro-5H-cyclopenta[b]pyridine-3-carboxamide (isomer 1) | 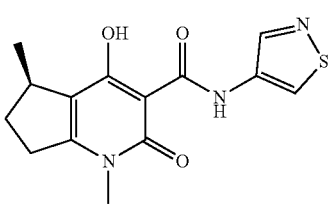 OR enantiomer | 306.3 |
| 41 | 4-Hydroxy-N-isothiazol-4-yl-1,5-dimethyl-2-oxo-6,7-dihydro-5H-cyclopenta[b]pyridine-3-carboxamide (isomer 2) | 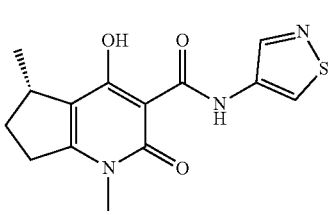 OR enantiomer | 306.3 |

TABLE 4-continued

Examples 16 to 53

| Ex No. | Chemical Name | Structure | ES/MS (m/z) (M + H) |
|---|---|---|---|
| 42 | 4-Hydroxy-1,6,6-trimethyl-2-oxo-N-(2-pyridyl)-5,7-dihydrocyclopenta[b]pyridine-3-carboxamide | 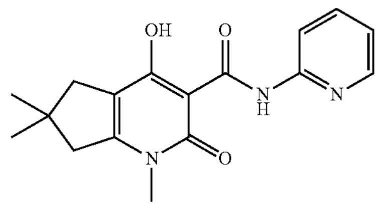 [SMILES: Cn1c2c(c(O)c(C(=O)Nc3ccccn3)c1=O)CC(C)(C)C2] | 314.2 |
| 43 | N-(5-Fluoropyrimidin-2-yl)-4-hydroxy-1,5,5-trimethyl-2-oxo-6,7-dihydrocyclopenta[b]pyridine-3-carboxamide | 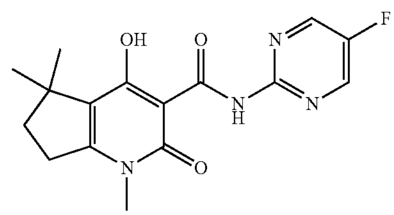 [SMILES: Cn1c2c(c(O)c(C(=O)Nc3ncc(F)cn3)c1=O)C(C)(C)CC2] | 332.9 |
| 44 | N-(5-Fluoro-2-pyridyl)-4-hydroxy-1,5,5-trimethyl-2-oxo-6,7-dihydrocyclopenta[b]pyridine-3-carboxamide | 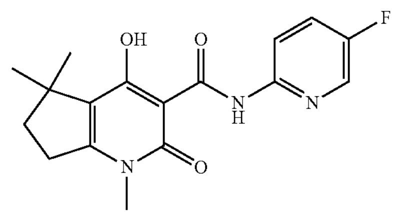 [SMILES: Cn1c2c(c(O)c(C(=O)Nc3ccc(F)cn3)c1=O)C(C)(C)CC2] | 332.0 |
| 45 | 1,6,6-Trimethyl-2-oxo-N-(2-pyridyl)-5,7-dihydrocyclopenta[b]pyridine-3-carboxamide | 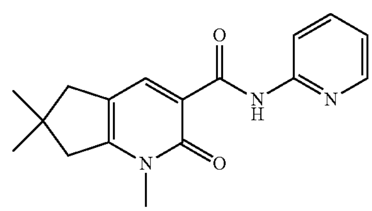 [SMILES: Cn1c2c(cc(C(=O)Nc3ccccn3)c1=O)CC(C)(C)C2] | 298.3 |
| 46 | 1,5,5-Trimethyl-2-oxo-N-pyrimidin-2-yl-6,7-dihydrocyclopenta[b]pyridine-3-carboxamide | 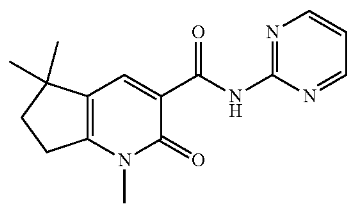 [SMILES: Cn1c2c(cc(C(=O)Nc3ncccn3)c1=O)C(C)(C)CC2] | 299.3 |
| 47 | 1,6,6-Trimethyl-2-oxo-N-phenyl-5,7-dihydrocyclopenta[b]pyridine-3-carboxamide | 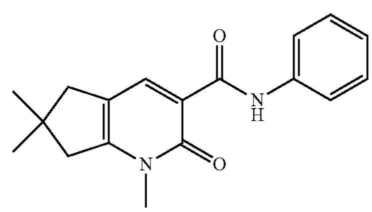 [SMILES: Cn1c2c(cc(C(=O)Nc3ccccc3)c1=O)CC(C)(C)C2] | 297.2 |
| 48 | N-(5-Fluoro-2-pyridyl)-1,6,6-trimethyl-2-oxo-5,7-dihydrocyclopenta[b]pyridine-3-carboxamide | 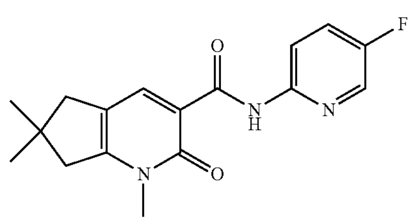 [SMILES: Cn1c2c(cc(C(=O)Nc3ccc(F)cn3)c1=O)CC(C)(C)C2] | 316.0 |

TABLE 4-continued

| | Examples 16 to 53 | | |
|---|---|---|---|
| Ex No. | Chemical Name | Structure | ES/MS (m/z) (M + H) |
| 49 | N-(5-Fluoro-2-pyridyl)-1,6,6-trimethyl-2-oxo-7,8-dihydro-5H-quinoline-3-carboxamide | 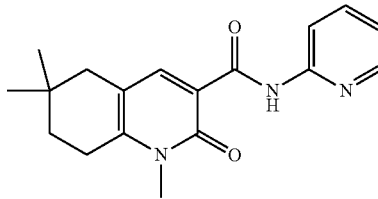 | 330.2 |
| 50 | 1,6,6-Trimethyl-N-(2-methyl-1,3-benzoxazol-6-yl)-2-oxo-7,8-dihydro-5H-quinoline-3-carboxamide | 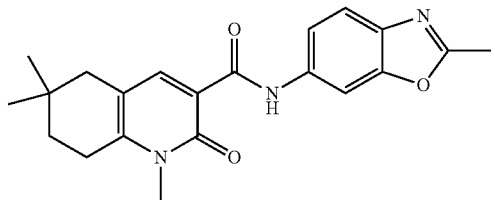 | 366.2 |
| 51 | 1,7,7-Trimethyl-2-oxo-N-phenyl-5,8-dihydropyrano[4,3-b]pyridine-3-carboxamide | 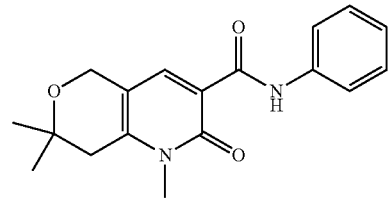 [SMILES: Cn1c2c(cc(C(=O)Nc3ccccc3)c1=O)COC(C)(C)C2] | 313.2 |
| 52 | 1,7-Dimethyl-2-oxo-N-phenyl-6,7-dihydro-5H-cyclopenta[b]pyridine-3-carboxamide | 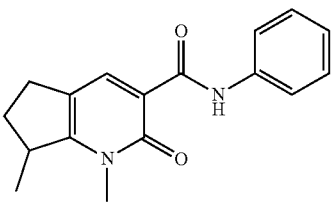 [SMILES: CC1CCc2cc(C(=O)Nc3ccccc3)c(=O)n(C)c21] | 283.0 |
| 53 | 1,5-Dimethyl-2-oxo-N-phenyl-5,6,7,8-tetrahydroquinoline-3-carboxamide | 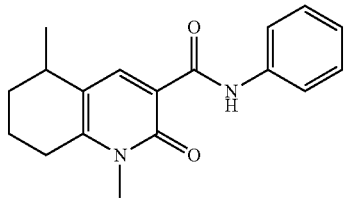 [SMILES: CC1CCCc2c1cc(C(=O)Nc1ccccc1)c(=O)n2C] | 297.3 |

Example 54 & 55

N-(5-Fluorothiazol-2-yl)-1,5-dimethyl-2-oxo-6,7-dihydro-5H-cyclopenta[b]pyridine-3-carboxamide (Isomer 1) and N-(5-Fluorothiazol-2-yl)-1,5-dimethyl-2-oxo-6,7-dihydro-5H-cyclopenta[b]pyridine-3-carboxamide (Isomer 2)

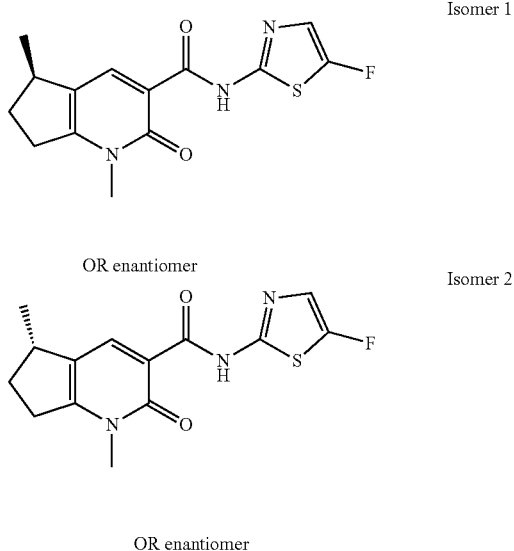

N-(5-Fluorothiazol-2-yl)-1,5-dimethyl-2-oxo-6,7-dihydro-5H-cyclopenta[b]pyridine-3-carboxamide (496 mg) is purified via chiral SFC chromatography (0.1% NH₄OH-EtOH; Column: DAICEL CHIRALCEL® OJ (250 mm×30 mm, 10 um); begin B: 35%; End B: 35%; Flow Rate: 80 mL/min.) to give isomer 1 as the first-off the column (200 mg) ES/MS (m/z): 308.3 (M+H). $^1$H NMR (400.13 MHz, d6-DMSO): 13.44 (s, 1H), 8.34 (s, 1H), 7.36 (d, J=2.5 Hz, 1H), 3.58 (s, 3H), 3.25-3.19 (m, 3H), 2.41-2.32 (m, 1H), 1.69-1.63 (m, 1H), 1.24 (d, J=6.8 Hz, 3H), followed by isomer 2 (188 mg). ES/MS (m/z): 308.3 (M+H). $^1$H NMR (400.13 MHz, d6-DMSO): 13.44 (s, 1H), 8.34 (s, 1H), 7.36 (d, J=2.5 Hz, 1H), 3.58 (s, 3H), 3.25-3.19 (m, 3H), 2.41-2.32 (m, 1H), 1.69-1.63 (m, 1H), 1.24 (d, J=6.8 Hz, 3H).

The following compounds in Table 5 are prepared in a manner essentially analogous to the method of preparing N-(5-fluorothiazol-2-yl)-1,5-dimethyl-2-oxo-6,7-dihydro-5H-cyclopenta[b]pyridine-3-carboxamide (isomer-1) and N-(5-fluorothiazol-2-yl)-1,5-dimethyl-2-oxo-6,7-dihydro-5H-cyclopenta[b]pyridine-3-carboxamide (isomer-2) (Example 54 & 55) using the appropriate reagents and adjusting the reaction time to determine completion of the reaction.

TABLE 5

Examples 56 to 71 and 112 to 115

| Ex No. | Chemical Name | Structure | ES/MS (m/z) (M + H) |
|---|---|---|---|
| 56 | N-(5-Fluoro-2-pyridyl)-1,5-dimethyl-2-oxo-6,7-dihydro-5H-cyclopenta[b]pyridine-3-carboxamide (isomer 1) | 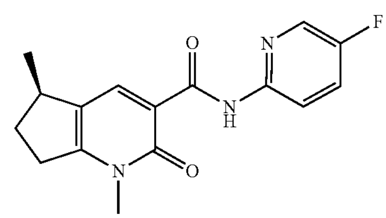 | 302.3 |
| 57 | N-(5-Fluoro-2-pyridyl)-1,5-dimethyl-2-oxo-6,7-dihydro-5H-cyclopenta[b]pyridine-3-carboxamide (isomer 2) | 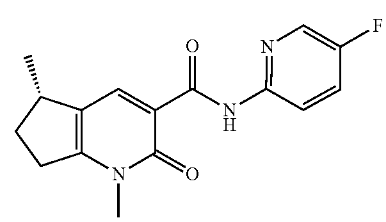 | 302.3 |

TABLE 5-continued

Examples 56 to 71 and 112 to 115

| Ex No. | Chemical Name | Structure | ES/MS (m/z) (M + H) |
|---|---|---|---|
| 58 | 1,5-Dimethyl-2-oxo-N-[5-(trifluoromethyl)-2-pyridyl]-6,7-dihydro-5H-cyclopenta[b]pyridine-3-carboxamide (isomer 1) | OR enantiomer | 352.3 |
| 59 | 1,5-Dimethyl-2-oxo-N-[5-(trifluoromethyl)-2-pyridyl]-6,7-dihydro-5H-cyclopenta[b]pyridine-3-carboxamide (isomer -2) | OR enantiomer | 352.3 |
| 60 | N-Cyclopentyl-1,5-dimethyl-2-oxo-6,7-dihydro-5H-cyclopenta[b]pyridine-3-carboxamide (isomer-1) | OR enantiomer | 275.3 |
| 61 | N-Cyclopentyl-1,5-dimethyl-2-oxo-6,7-dihydro-5H-cyclopenta[b]pyridine-3-carboxamide (isomer-2) | OR enantiomer | 275.3 |
| 62 | 1,5-Dimethyl-2-oxo-N-thiazol-2-yl-6,7-dihydro-5H-cyclopenta[b]pyridine-3-carboxamide (isomer-1) | OR enantiomer | 290.3 |

TABLE 5-continued

Examples 56 to 71 and 112 to 115

| Ex No. | Chemical Name | Structure | ES/MS (m/z) (M + H) |
|---|---|---|---|
| 63 | 1,5-Dimethyl-2-oxo-N-thiazol-2-yl-6,7-dihydro-5H-cyclopenta[b]pyridine-3-carboxamide (isomer -2) | OR enantiomer | 290.3 |
| 64 | 1,5-Dimethyl-2-oxo-N-[5-(trifluoromethyl)pyrimidin-2-yl]-6,7-dihydro-5H-cyclopenta[b]pyridine-3-carboxamide (isomer -1) | OR enantiomer | 353.3 |
| 65 | 1,5-Dimethyl-2-oxo-N-[5-(trifluoromethyl)pyrimidin-2-yl]-6,7-dihydro-5H-cyclopenta[b]pyridine-3-carboxamide (isomer -2) | OR enantiomer | 353.3 |
| 66 | (5R)-1,5-Dimethyl-2-oxo-N-phenyl-6,7-dihydro-5H-cyclopenta[b]pyridine-3-carboxamide | 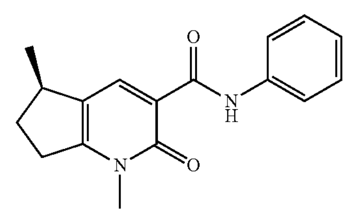 [SMILES: C[C@@H]1CCc2c1cc(C(=O)Nc1ccccc1)c(=O)n2C] | 383.3 |
| 67 | (5S)-1,5-Dimethyl-2-oxo-N-phenyl-6,7-dihydro-5H-cyclopenta[b]pyridine-3-carboxamide | 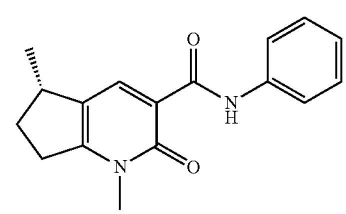 [SMILES: C[C@H]1CCc2c1cc(C(=O)Nc1ccccc1)c(=O)n2C] | 383.3 |
| 68 | 1,5-Dimethyl-2-oxo-N-phenyl-5,6,7,8-tetrahydroquinoline-3-carboxamide (isomer 1) | OR enantiomer | 297.3 |

TABLE 5-continued

Examples 56 to 71 and 112 to 115

| Ex No. | Chemical Name | Structure | ES/MS (m/z) (M + H) |
|---|---|---|---|
| 69 | 1,5-Dimethyl-2-oxo-N-phenyl-5,6,7,8-tetrahydroquinoline-3-carboxamide (isomer 2) | OR enantiomer | 297.3 |
| 70 | 1,6-Dimethyl-2-oxo-N-phenyl-5,6,7,8-tetrahydroquinoline-3-carboxamide (isomer 1) | OR enantiomer | 297.3 |
| 71 | 1,6-Dimethyl-2-oxo-N-phenyl-5,6,7,8-tetrahydroquinoline-3-carboxamide (isomer 2) | OR enantiomer | 297.3 |
| 112 | N-(5-fluoropyrimidin-2-yl)-5-isopropyl-1-methyl-2-oxo-6,7-dihydro-5H-cyclopenta[b]pyridine-3-carboxamide (isomer 1) | OR enantiomer | 331.1 |
| 113 | N-(5-fluoropyrimidin-2-yl)-5-isopropyl-1-methyl-2-oxo-6,7-dihydro-5H-cyclopenta[b]pyridine-3-carboxamide (isomer 2) | OR enantiomer | 331.1 |
| 114 | 5-ethyl-N-(5-fluoropyrimidin-2-yl)-1-methyl-2-oxo-6,7-dihydro-5H-cyclopenta[b]pyridine-3-carboxamide (isomer 1) | OR enantiomer | 317.1 |

TABLE 5-continued

Examples 56 to 71 and 112 to 115

| Ex No. | Chemical Name | Structure | ES/MS (m/z) (M + H) |
|---|---|---|---|
| 115 | 5-ethyl-N-(5-fluoropyrimidin-2-yl)-1-methyl-2-oxo-6,7-dihydro-5H-cyclopenta[b]pyridine-3-carboxamide (isomer 2) | OR enantiomer | 317.1 |

Example 72

(5S)—N-(1H-Indol-2-yl)-1,5-dimethyl-2-oxo-6,7-dihydro-5H-cyclopenta[b]pyridine-3-carboxamide

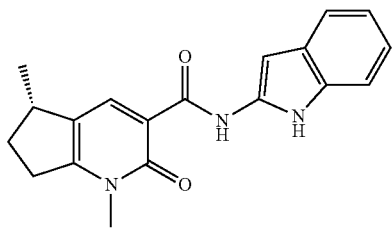 [SMILES: C[C@H]1CCc2c1cc(C(=O)Nc1cc3ccccc3[nH]1)c(=O)n2C]

(5S)-1,5-Dimethyl-2-oxo-6,7-dihydro-5H-cyclopenta[b]pyridine-3-carboxylic acid (90 mg, 0.434 mmol), 2,3-dihydro-1H-indol-2-imine hydrochloride (120 mg, 0.676 mmol), and NMI (165 mg, 2 mmol) are dissolved in ACN (4 mL). TCFH (150 mg, 0.524 mmol) is added and stirred at 20° C. for 16 h. After this time volatiles are evaporated under reduced pressure and the residue purified via silica gel chromatography (20 g, 0-100% EtOAc in petroleum ether) to give the title product as a white solid (368.3 mg, 1.21 mmol, 84%). ES/MS (m/z): 322.0 (M+H). $^1$H NMR (400.14 MHz, d6-DMSO): 12.70 (s, 1H), 11.40 (s, 1H), 8.36 (s, 1H), 7.41-7.39 (m, 1H), 7.32 (d, J=7.8 Hz, 1H), 7.01-6.93 (m, 2H), 6.48 (d, J=1.3 Hz, 1H), 3.59 (s, 3H), 3.26-3.25 (m, 1H), 3.13-3.08 (m, 2H), 2.44-2.42 (m, 1H), 1.70-1.64 (m, 1H), 1.25 (d, J=6.9 Hz, 3H).

The following compounds in Table 6 are prepared in a manner essentially analogous to the method of preparing (5S)—N-(1H-indol-2-yl)-1,5-dimethyl-2-oxo-6,7-dihydro-5H-cyclopenta[b]pyridine-3-carboxamide (Example 72) using the appropriate reagents and adjusting the reaction time to determine completion of the reaction.

TABLE 6

Examples 73 to 76

| Ex No. | Chemical Name | Structure | ES/MS (m/z) (M + H) |
|---|---|---|---|
| 73 | (5R)-N-(1H-indol-2-yl)-1,5-dimethyl-2-oxo-6,7-dihydro-5H-cyclopenta[b]pyridine-3-carboxamide | 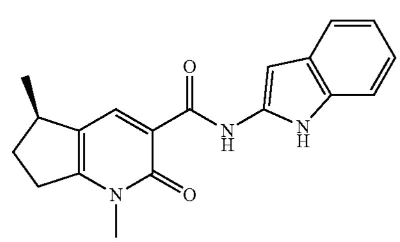 [SMILES: C[C@@H]1CCc2c1cc(C(=O)Nc1cc3ccccc3[nH]1)c(=O)n2C] | 322.0 |
| 74 | (5R)-1,5-Dimethyl-N-oxazol-2-yl-2-oxo-6,7-dihydro-5H-cyclopenta[b]pyridine-3-carboxamide | 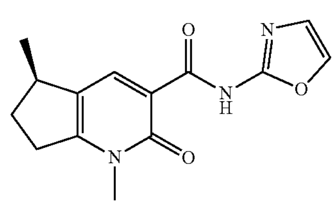 [SMILES: C[C@@H]1CCc2c1cc(C(=O)Nc1ncco1)c(=O)n2C] | 274.3 |

TABLE 6-continued

Examples 73 to 76

| Ex No. | Chemical Name | Structure | ES/MS (m/z) (M + H) |
|---|---|---|---|
| 75 | (5S)-1,5-Dimethyl-N-oxazol-2-yl-2-oxo-6,7-dihydro-5H-cyclopenta[b]pyridine-3-carboxamide | 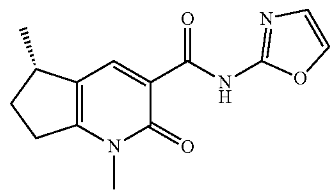 [SMILES: C[C@H]1CCc2c1cc(C(=O)Nc1ncco1)c(=O)n2C] | 274.3 |
| 76 | 1,6-Dimethyl-2-oxo-N-phenyl-5,6,7,8-tetrahydroquinoline-3-carboxamide | 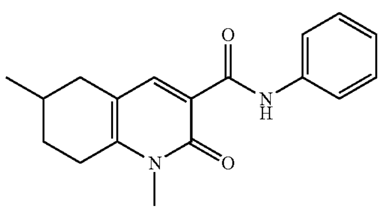 [SMILES: CC1CCc2c(cc(C(=O)Nc3ccccc3)c(=O)n2C)C1] | 297.3 |

Example 77 & 78

1,6-Dimethyl-2-oxo-N-phenyl-6,7-dihydro-5H-cyclopenta[b]pyridine-3-carboxamide (Isomer 1) and 1,6-Dimethyl-2-oxo-N-phenyl-6,7-dihydro-5H-cyclopenta[b]pyridine-3-carboxamide (Isomer 2)

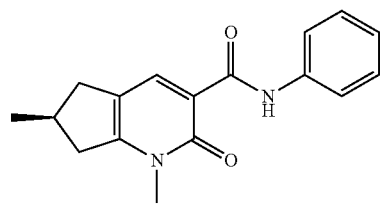

Isomer 1

OR enantiomer

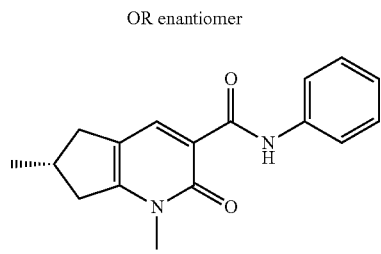

Isomer 2

OR enantiomer

Step A. 3-Methylcyclopentanone (4.4 mL, 38.9 mmol) is dissolved in a 2M solution of methylamine in THF (100 mL). Sodium sulfate (16.8 g, 116 mmol) is added and stirred for 18 h. The mixture is concentrated down to 5 mL total volume to give (Z)—N,3-dimethylcyclopentanimine residue. ES/MS (m/z): 111.1 (M+).

Step B: The residue from step A (4.3 g, 38.7 mmol) is dissolved in MeOH (100 mL) and dimethyl methoxymethylenemalonate (13.8 g, 77.7 mmol) added and heated via a microwave to 140° C. for 3 h. The mixture is concentrated and purified via silica gel chromatography (0-10% MeOH in DCM) to give methyl 1,6-dimethyl-2-oxo-6,7-dihydro-5H-cyclopenta[b]pyridine-3-carboxylate and methyl 1,5-dimethyl-2-oxo-6,7-dihydro-5H-cyclopenta[b]pyridine-3-carboxylate as a mixture of regio and stereoisomers (7.17 g, 32.4 mmol, 83%). ES/MS (m/z): 222.0 (M+). $^1$H NMR (399.80 MHz, CDCl$_3$): 1.17 (d, J=6.8 Hz, 3H), 1.24-1.21 (m, 3H), 2.42-2.34 (m, 2H), 2.55 (dd, J=6.5, 17.3 Hz, 1H), 2.70-2.61 (m, 2H), 2.99-2.87 (m, 3H), 3.15-3.07 (m, 2H), 3.49 (d, J=5.3 Hz, 6H), 3.86 (d, J=3.9 Hz, 6H), 8.03 (d, J=2.3 Hz, 2H).

Step C: The product from step B (7.17 g, 32.4 mmol) is dissolved in MeOH (150 mL) and 5M aqueous sodium hydroxide solution is added and stirred for 18 h. The reaction is quenched with 5N aqueous HCl solution and extracted with a 3:1 mixture of DCM/isopropanol. The organic layers are combined and washed with brine, dried over anhydrous magnesium sulfate, filtered, and evaporated under vacuum to give 1,6-dimethyl-2-oxo-6,7-dihydro-5H-cyclopenta[b]pyridine-3-carboxylic acid and 1,5-dimethyl-2-oxo-6,7-dihydro-5H-cyclopenta[b]pyridine-3-carboxylic acid as a mixture of regio and stereoisomers (5.0 g, 24 mmol, 74%). ES/MS (m/z): 208.0 (M+).

Step D: The product from step C (300 mg, 1.45 mmol) is dissolved in DMF (10 mL). Aniline (0.3 mL, 3.3 mmol), DIEA (800 µL, 4.59 mmol), and T$_3$P (50% by mass in dimethylformamide, 1.8 mL, 3.0 mmol) are added and heated to 100° C. in a microwave reactor for 1 h. The mixture is poured into a saturated solution of sodium bicarbonate (50 mL) and extracted with EtOAc (50 mL×3). The organic layers are combined and washed with brine, dried over anhydrous magnesium sulfate, filtered, evaporated under vacuum, and then purified via silica gel chromatography (0-100% EtOAc in hexanes) to give 1,6-dimethyl-2-oxo-N-phenyl-6,7-dihydro-5H-cyclopenta[b]pyridine-3-carboxamide and 1,5-dimethyl-2-oxo-N-phenyl-6,7-dihydro-5H-cyclopenta[b]pyridine-3-carboxamide as a mixture of regio and stereoisomers (94 mg, 0.33 mmol, 23%). ES/MS (m/z): 283.0 (M+). $^1$H NMR (399.80 MHz, CDCl$_3$): 1.21 (d, J=6.8 Hz, 4H), 1.29 (d, J=6.8 Hz, 2H), 2.52-2.43 (m, 2H), 2.60 (dd, J=6.5, 17.1 Hz, 1H), 2.75-2.66

(m, 1H), 3.01-2.90 (m, 1H), 3.18-3.03 (m, 1H), 3.22 (q, J=7.2 Hz, 2H), 3.60 (d, J=6.0 Hz, 6H), 7.10 (td, J=7.4, 1.1 Hz, 2H), 7.38-7.33 (m, 4H), 7.79-7.76 (m, 4H), 8.50 (d, J=10.3 Hz, 2H), 12.17 (d, J=4.9 Hz, 2H).

Step E: Examples 77 & 78: The product from step D (342 mg) is purified via chiral column chromatography (Chiralpak AD-H, 4.6×150 nm, 40% EtOH/CO$_2$, 5 mL/min, 225 nm) to give isomer-1 as the first elution (86.6 mg), ES/MS (m/z): 283.0 (M+). $^1$H NMR (399.80 MHz, d6-DMSO): 1.14 (d, J=6.7 Hz, 3H), 2.47-2.42 (m, 1H), 2.74-2.60 (m, 2H), 3.03 (dd, J=8.1, 15.0 Hz, 1H), 3.31-3.23 (m, 1H), 3.56 (s, 3H), 7.12-7.07 (m, 1H), 7.38-7.32 (m, 2H), 7.70 (dd, J=1.0, 8.6 Hz, 2H), 8.34 (s, 1H), 12.32 (s, 1H); followed by isomer-2 (82 mg). ES/MS (m/z): 283.0 (M+). $^1$H NMR (399.80 MHz, d6-DMSO): 1.14 (d, J=6.7 Hz, 3H), 2.47-2.42 (m, 1H), 2.74-2.60 (m, 2H), 3.03 (dd, J=8.1, 15.0 Hz, 1H), 3.31-3.23 (m, 1H), 3.56 (s, 3H), 7.12-7.07 (m, 1H), 7.38-7.32 (m, 2H), 7.70 (dd, J=1.0, 8.6 Hz, 2H), 8.34 (s, 1H), 12.32 (s, 1H). (3$^{rd}$ elution is example 37 and 4$^{th}$ elution is example 38).

The following compounds in Table 7 are prepared in a manner essentially analogous to the method of preparing 1,6-dimethyl-2-oxo-N-phenyl-6,7-dihydro-5H-cyclopenta[b]pyridine-3-carboxamide (isomer-1) and 1,6-dimethyl-2-oxo-N-phenyl-6,7-dihydro-5H-cyclopenta[b]pyridine-3-carboxamide (isomer-2) (Example 77 & 78) using the appropriate reagents and adjusting the reaction time to determine completion of the reaction.

TABLE 7

Examples 79 to 82

| Ex No. | Chemical Name | Structure | ES/MS (m/z) (M + H) |
|---|---|---|---|
| 79 | 1,6-Dimethyl-2-oxo-N-pyrimidin-2-yl-6,7-dihydro-5H-cyclopenta[b]pyridine-3-carboxamide | 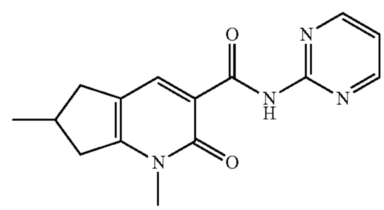 [SMILES: CC1Cc2cc(C(=O)Nc3ncccn3)c(=O)n(C)c2C1] | 285.1 |
| 80 | 1,5-Dimethyl-2-oxo-N-pyrimidin-2-yl-6,7-dihydro-5H-cyclopenta[b]pyridine-3-carboxamide (isomer 2) | OR enantiomer | 285.1 |
| 81 | 1,6-Dimethyl-2-oxo-N-phenyl-6,7-dihydro-5H-cyclopenta[b]pyridine-3-carboxamide | 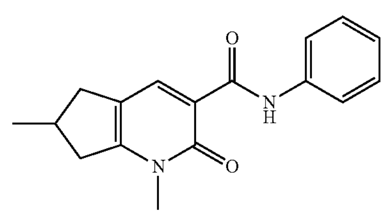 [SMILES: CC1Cc2cc(C(=O)Nc3ccccc3)c(=O)n(C)c2C1] | 283.1 |
| 82 | 1,5-Dimethyl-2-oxo-N-pyrimidin-2-yl-6,7-dihydro-5H-cyclopenta[b]pyridine-3-carboxamide (isomer 1) | OR enantiomer | 285.2 |

Examples 83 & 84 & 85 & 86

4-Hydroxy-1,6-dimethyl-2-oxo-N-pyrimidin-2-yl-6,7-dihydro-5H-cyclopenta[b]pyridine-3-carboxamide (Isomer 1), 4-Hydroxy-1,6-dimethyl-2-oxo-N-pyrimidin-2-yl-6,7-dihydro-5H-cyclopenta[b]pyridine-3-carboxamide (Isomer 2), 4-Hydroxy-1,5-dimethyl-2-oxo-N-pyrimidin-2-yl-6,7-dihydro-5H-cyclopenta[b]pyridine-3-carboxamide (Isomer 1), and 4-Hydroxy-1,5-dimethyl-2-oxo-N-pyrimidin-2-yl-6,7-dihydro-5H-cyclopenta[b]pyridine-3-carboxamide (Isomer 2)

Isomer 1

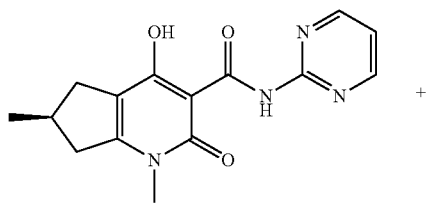

OR enantiomer

Isomer 2

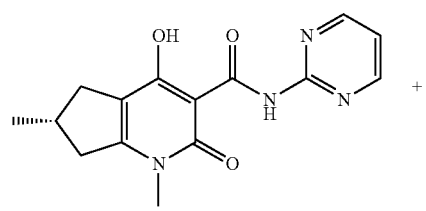

OR enantiomer

Isomer 1

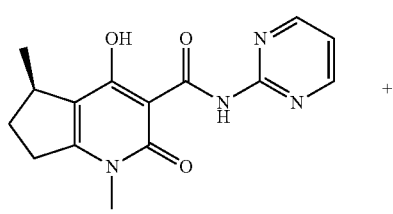

OR enantiomer

Isomer 2

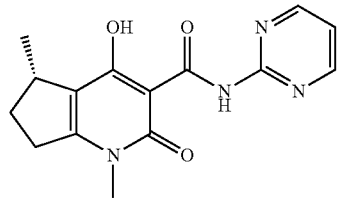

OR enantiomer

A mixture of 4-hydroxy-1,5-dimethyl-2-oxo-6,7-dihydro-5H-cyclopenta[b]pyridine-3-carboxylic acid and 4-hydroxy-1,6-dimethyl-2-oxo-6,7-dihydro-5H-cyclopenta[b]pyridine-3-carboxylic acid (549 mg, 5.7 mmol) is dissolved in DCE (10 mL). T$_3$P (1.7 mol/L in EtOAc) (4.89 g, 7.7 mmol) is added, and the mixture heated to 80° C. for 2 h. After this time, the volatiles are evaporated under reduced pressure and the residue purified via silica gel chromatography (20 g, and EtOAc in petroleum ether). The residue is further purified via chiral column (DAICEL CHIRALCEL OD, 250 mm×30 mm, 10 um; mobile phase: 0.1% NH$_{40}$H-EtOH; B %:40%-40%). First-off the column is 4-hydroxy-1,6-dimethyl-2-oxo-N-pyrimidin-2-yl-6,7-dihydro-5H-cyclopenta[b]pyridine-3-carboxamide (isomer 1) as a white solid (150.66 mg, 0.5 mmol, 27%). ES/MS (m/z): 301.1 (M+H). $^1$H NMR (400.15 MHz, d6-DMSO): 15.15 (s, 1H), 13.20 (s, 1H), 8.73 (d, J=4.9 Hz, 2H), 7.28 (t, J=4.9 Hz, 1H), 3.43 (s, 3H), 3.31-3.29 (m, 1H), 2.99-2.93 (m, 1H), 2.71-2.63 (m, 2H), 2.37-2.30 (m, 1H), 1.14 (d, J=6.8 Hz, 3H). Next off is 4-hydroxy-1,6-dimethyl-2-oxo-N-pyrimidin-2-yl-6,7-dihydro-5H-cyclopenta[b]pyridine-3-carboxamide (isomer 2) as a white solid (217 mg, 0.72 mmol, 39%). ES/MS (m/z): 301.3 (M+H). $^1$H NMR (400.15 MHz, d6-DMSO): 15.15 (s, 1H), 13.20 (s, 1H), 8.73 (d, J=4.9 Hz, 2H), 7.28 (t, J=4.9 Hz, 1H), 3.43 (s, 3H), 3.31-3.29 (m, 1H), 2.99-2.93 (m, 1H), 2.71-2.63 (m, 2H), 2.37-2.30 (m, 1H), 1.14 (d, J=6.8 Hz, 3H). Third off the column is 4-hydroxy-1,5-dimethyl-2-oxo-N-pyrimidin-2-yl-6,7-dihydro-5H-cyclopenta[b]pyridine-3-carboxamide (isomer 1) as a white solid (78.5 mg, 0.26 mmol, 14%). ES/MS (m/z): 301.3 (M+H). $^1$H NMR (400.15 MHz, d6-DMSO): 15.33-15.30 (m, 1H), 13.22 (s, 1H), 8.73 (d, J=4.8 Hz, 2H), 7.28 (t, J=4.9 Hz, 1H), 3.44 (s, 3H), 3.31-3.26 (m, 1H), 3.19-3.16 (m, 1H), 3.03-2.99 (m, 1H), 2.35-2.30 (m, 1H), 1.69-1.61 (m, 1H), 1.22 (d, J=6.9 Hz, 3H). Finally, 4-hydroxy-1,5-dimethyl-2-oxo-N-pyrimidin-2-yl-6,7-dihydro-5H-cyclopenta[b]pyridine-3-carboxamide (isomer 2) as a white solid (77 mg, 0.25 mmol, 14%). ES/MS (m/z): 301.1 (M+H). $^1$H NMR (400.15 MHz, d6-DMSO): 15.33-15.30 (m, 1H), 13.22 (s, 1H), 8.73 (d, J=4.8 Hz, 2H), 7.28 (t, J=4.9 Hz, 1H), 3.44 (s, 3H), 3.31-3.26 (m, 1H), 3.19-3.16 (m, 1H), 3.03-2.99 (m, 1H), 2.35-2.30 (m, 1H), 1.69-1.61 (m, 1H), 1.22 (d, J=6.9 Hz, 3H).

The following compounds in Table 8 are prepared in a manner essentially analogous to the method of preparing 4-hydroxy-1,6-dimethyl-2-oxo-N-pyrimidin-2-yl-6,7-dihydro-5H-cyclopenta[b]pyridine-3-carboxamide and isomers, as well 4-hydroxy-1,5-dimethyl-2-oxo-N-pyrimidin-2-yl-6,7-dihydro-5H-cyclopenta[b]pyridine-3-carboxamide isomers (Example 86 & 87 & 88 & 89) using the appropriate reagents and adjusting the reaction time to determine completion of the reaction.

TABLE 8

Examples 87 to 102

| Ex No. | Chemical Name | Structure | ES/MS (m/z) (M + H) |
|---|---|---|---|
| 87 | 4-Hydroxy-1,6-dimethyl-2-oxo-N-(2-pyridyl)-6,7-dihydro-5H-cyclopenta[b]pyridine-3-carboxamide (isomer 1) | OR enantiomer | 299.9 |
| 88 | 4-Hydroxy-1,6-dimethyl-2-oxo-N-(2-pyridyl)-6,7-dihydro-5H-cyclopenta[b]pyridine-3-carboxamide (isomer 2) | OR enantiomer | 300.0 |
| 89 | 4-Hydroxy-1,5-dimethyl-2-oxo-N-(2-pyridyl)-6,7-dihydro-5H-cyclopenta[b]pyridine-3-carboxamide (isomer 1) | OR enantiomer | 299.9 |
| 90 | 4-Hydroxy-1,5-dimethyl-2-oxo-N-(2-pyridyl)-6,7-dihydro-5H-cyclopenta[b]pyridine-3-carboxamide (isomer 2) | OR enantiomer | 299.9 |
| 91 | N-(3-Fluoro-2-pyridyl)-4-hydroxy-1,5-dimethyl-2-oxo-6,7-dihydro-5H-cyclopenta[b]pyridine-3-carboxamide (isomer 1) | OR enantiomer | 318.3 |
| 92 | N-(3-Fluoro-2-pyridyl)-4-hydroxy-1,5-dimethyl-2-oxo-6,7-dihydro-5H-cyclopenta[b]pyridine-3-carboxamide (isomer 2) | OR enantiomer | 318.3 |

TABLE 8-continued

Examples 87 to 102

| Ex No. | Chemical Name | Structure | ES/MS (m/z) (M + H) |
|---|---|---|---|
| 93 | N-(5-Chloropyrimidin-2-yl)-4-hydroxy-1,5-dimethyl-2-oxo-6,7-dihydro-5H-cyclopenta[b]pyridine-3-carboxamide (isomer 1) | OR enantiomer | 335.3 |
| 94 | N-(5-Chloropyrimidin-2-yl)-4-hydroxy-1,5-dimethyl-2-oxo-6,7-dihydro-5H-cyclopenta[b]pyridine-3-carboxamide (isomer 2) | OR enantiomer | 335.3 |
| 95 | N-(5-Fluoropyrimidin-2-yl)-4-hydroxy-1,5-dimethyl-2-oxo-6,7-dihydro-5H-cyclopenta[b]pyridine-3-carboxamide (isomer 1) | OR enantiomer | 319.3 |
| 96 | N-(5-Fluoropyrimidin-2-yl)-4-hydroxy-1,5-dimethyl-2-oxo-6,7-dihydro-5H-cyclopenta[b]pyridine-3-carboxamide (isomer 2) | OR enantiomer | 319.3 |
| 97 | 4-Hydroxy-1,5-dimethyl-2-oxo-N-[5-(trifluoromethyl)pyrimidin-2-yl]-6,7-dihydro-5H-cyclopenta[b]pyridine-3-carboxamide (isomer 1) | OR enantiomer | 369.3 |

TABLE 8-continued

Examples 87 to 102

| Ex No. | Chemical Name | Structure | ES/MS (m/z) (M + H) |
|---|---|---|---|
| 98 | 4-Hydroxy-1,5-dimethyl-2-oxo-N-[5-(trifluoromethyl)pyrimidin-2-yl]-6,7-dihydro-5H-cyclopenta[b]pyridine-3-carboxamide (isomer 2) | OR enantiomer | 369.3 |
| 99 | N-(5-Fluoro-2-pyridyl)-4-hydroxy-1,5-dimethyl-2-oxo-6,7-dihydro-5H-cyclopenta[b]pyridine-3-carboxamide (isomer 1) | OR enantiomer | 318.3 |
| 100 | N-(5-Fluoro-2-pyridyl)-4-hydroxy-1,5-dimethyl-2-oxo-6,7-dihydro-5H-cyclopenta[b]pyridine-3-carboxamide (isomer 2) | OR enantiomer | 318.3 |
| 101 | 4-Hydroxy-N-(5-methoxypyrimidin-2-yl)-1,5-dimethyl-2-oxo-6,7-dihydro-5H-cyclopenta[b]pyridine-3-carboxamide (isomer 1) | OR enantiomer | 331.3 |
| 102 | 4-Hydroxy-N-(5-methoxypyrimidin-2-yl)-1,5-dimethyl-2-oxo-6,7-dihydro-5H-cyclopenta[b]pyridine-3-carboxamide (isomer 2) | OR enantiomer | 331.3 |

Example 103

1-Methyl-2-oxo-N-pyrimidin-2-yl-5,6,7,8-tetrahydroquinoline-3-carboxamide

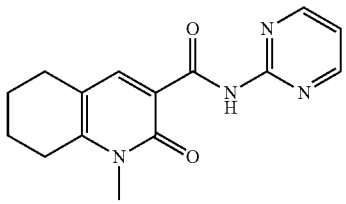 [SMILES: Cn1c2c(cc(C(=O)Nc3ncccn3)c1=O)CCCC2]

1-Methyl-2-oxo-1,2,5,6,7,8-hexahydro-3-quinolinecarboxylic acid (250 mg, 1.14 mmol) is dissolved in DMF (2.2 mL). 2-Aminopyrimidine (100 mg, 1.02 mmol), DIPEA (463 µL, 2.6 mmol), and HATU (499 mg, 1.31 mmol) are added and stirred at RT for 15 h. The mixture is purified via reverse phase HPLC to give the product (33 mg, 0.16 mmol, 11%). ES/MS (m/z): 285.0 (M+H). $^1$H NMR (400.13 MHz, d6-DMSO): 1.71-1.65 (m, 2H), 1.84-1.78 (m, 2H), 2.68-2.63 (m, 2H), 2.82 (t, J=6.3 Hz, 2H), 3.58 (s, 3H), 7.22 (t, J=4.8 Hz, 1H), 8.20 (s, 1H), 8.70 (d, J=4.8 Hz, 2H), 12.88 (s, 1H).

The following compounds in Table 9 are prepared in a manner essentially analogous to the method of preparing 1-methyl-2-oxo-N-pyrimidin-2-yl-5,6,7,8-tetrahydroquinoline-3-carboxamide (Example 103) using the appropriate reagents and adjusting the reaction time to determine completion of the reaction.

TABLE 9

Examples 104 to 109

| Ex No. | Chemical Name | Structure | ES/MS (m/z) (M + H) |
|---|---|---|---|
| 104 | 1-Methyl-2-oxo-N-phenyl-5,6,7,8-tetrahydroquinoline-3-carboxamide | 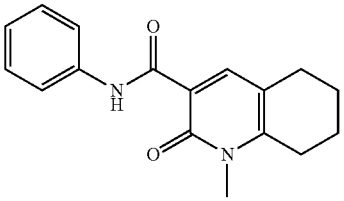 [SMILES: Cn1c2c(cc(C(=O)Nc3ccccc3)c1=O)CCCC2] | 283.0 |
| 105 | 1,6,6-Trimethyl-2-oxo-N-phenyl-7,8-dihydro-5H-quinoline-3-carboxamide | 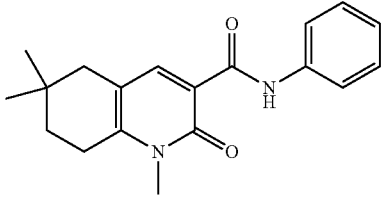 [SMILES: Cn1c2c(cc(C(=O)Nc3ccccc3)c1=O)CC(C)(C)CC2] | 311.2 |
| 106 | 1-Methyl-2-oxo-N-phenyl-7,8-dihydro-5H-pyrano[4,3-b]pyridine-3-carboxamide | 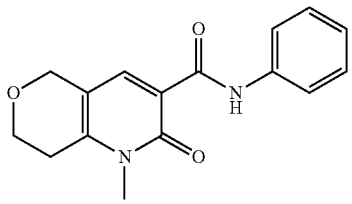 [SMILES: Cn1c2c(cc(C(=O)Nc3ccccc3)c1=O)COCC2] | 385.2 |
| 107 | 6-Ethyl-1-methyl-2-oxo-N-phenyl-7,8-dihydro-5H-1,6-naphthyridine-3-carboxamide | 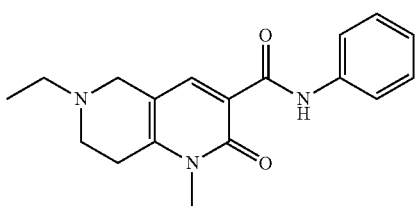 [SMILES: CCN1CCc2c(cc(C(=O)Nc3ccccc3)c(=O)n2C)C1] | 312.0 |
| 108 | 1-Methyl-2-oxo-N-phenyl-6,7-dihydro-5H-cyclopenta[b]pyridine-3-carboxamide | 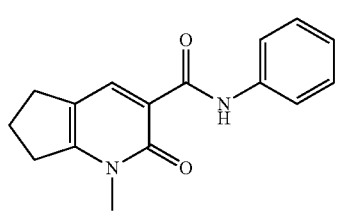 [SMILES: Cn1c2c(cc(C(=O)Nc3ccccc3)c1=O)CCC2] | 269.1 |

TABLE 9-continued

Examples 104 to 109

| Ex No. | Chemical Name | Structure | ES/MS (m/z) (M + H) |
|---|---|---|---|
| 109 | 1-Methyl-2-oxo-N-phenyl-6,7,8,9-tetrahydro-5H-cyclohepta[b]pyridine-3-carboxamide | 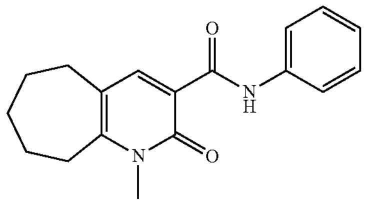 [SMILES: Cn1c2c(cc(C(=O)Nc3ccccc3)c1=O)CCCCC2] | 297.3 |

Example 110

4-Hydroxy-1,6,6-trimethyl-2-oxo-N-phenyl-7,8-dihydro-5H-quinoline-3-carboxamide

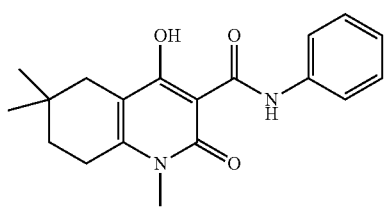 [SMILES: Cn1c2c(c(O)c(C(=O)Nc3ccccc3)c1=O)CC(C)(C)CC2]

Ethyl 4-hydroxy-1,3,6,6-tetramethyl-2-oxo-7,8-dihydro-5H-quinoline-3-carboxylate (181 mg, 0.62 mmol) is dissolved in toluene (3.5 mL). Aniline (0.1 mL, 1 mmol) is heated via microwave to 200° C. for 1 h. and concentrated under vacuum and purified via silica gel chromatography (0-50% EtOAc in hexanes) to give the title product (58.2 mg, 0.178 mmol, 29%). ES/MS (m/z): 327.2 (M+H). $^1$H NMR (399.80 MHz, CDCl$_3$): 1.03 (s, 6H), 1.65 (t, J=6.6 Hz, 2H), 2.37 (s, 2H), 2.68 (t, J=6.6 Hz, 2H), 3.54 (s, 3H), 7.17-7.13 (m, 1H), 7.39-7.35 (m, 3H), 7.70-7.68 (m, 2H), 12.60 (s, 1H).

Example 111

4-Hydroxy-N-isopentyl-1-methyl-2-oxo-5,6,7,8-tetrahydroquinoline-3-carboxamide

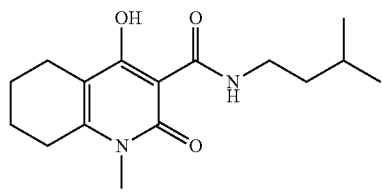 [SMILES: CC(C)CCNC(=O)c1c(O)c2c(n(C)c1=O)CCCC2]

4-Hydroxy-N-isopentyl-2-oxo-5,6,7,8-tetrahydro-1H-quinoline-3-carboxamide (45.8 mg, 0.165 mmol) is dissolved in DMF (1 mL) and MeOH (1 mL). Potassium carbonate (50 mg, 0.36 mmol) and iodomethane (23 μL, 0.34 mmol) are added and stirred for 24 h. The resulting mixture is purified via reverse phase HPLC to give the title product (37.3 mg, 0.128 mmol, 78%). ES/MS (m/z): 293.2 (M+H). $^1$H NMR (400.13 MHz, d6-DMSO): 0.91 (d, J=6.6 Hz, 6H), 1.42 (q, J=7.1 Hz, 2H), 1.66-1.58 (m, 3H), 1.79-1.73 (m, 2H), 2.39 (t, J=6.1 Hz, 2H), 2.72-2.67 (m, 2H). $^1$H NMR (400.13 MHz, d6-DMSO): 0.91 (d, J=6.6 Hz, 6H), 1.42 (q, J=7.1 Hz, 2H), 1.66-1.58 (m, 3H), 1.79-1.73 (m, 2H), 2.39 (t, J=6.1 Hz, 2H), 2.72-2.67 (m, 2H), 3.17 (d, J=5.3 Hz, 1H), 3.30 (d, J=5.3 Hz, 1H), 3.40 (s, 3H), 10.39 (t, J=5.5 Hz, 1H).

hAHR Nuclear Translocation Assay

Stable cell lines were established using Jump-In™ T-REx™ HEK293 Retargeting Kit (Life Technologies). hAhR cDNA was cloned into the pJTI R4 CMV-TO EGFP vector. The EGFP was cloned to the C-terminal of AHR to form AhR-EGFP chimera. The pJTI R4 CMV-TO AhR-EGFP vector was transfected using FuGENE® HD into Jump-In™ T-REx™ HEK293 cells. Transfected cells were selected using 2.5 mg/ml G418 for 10 to 14 days, then expanded, harvested, and suspended in freeze media (FBS with 8% DMSO) at 2×10$^7$ cells/mL, and aliquots were stored in liquid nitrogen. One day before the assay date, cells were thawed and resuspended in DMEM with 5% FBS in the presence of 1 μg/mL Doxycycline and plated into poly-L-Lysine coated CELLCARRIER-384 ULTRA Microplates (Perkin Elmer) at 12,000 to 15,000 cells per well and incubated at 37° C. and 5% CO$_2$ overnight. On the assay date, compound was serially diluted (1:2) into 384-well nunc plates with DMSO using acoustic dispensing (ECHO). The dose response was a 20-point curve. Compound was resuspended in 40 μL of DMEM plus 0.1% BSA. The culture media was damped and 25 μL of DMEM plus 0.1% BSA was added, then 25 μL of compound in DMEM plus 0.1% BSA was added into cell plates. Cells were incubated with compounds at 37° C. and 5% CO$_2$ for 45 min.

The final DMSO concentration was 0.2%. The media was damped after 45 minutes incubation. The cells were fixed with 40 μL of cold MeOH (−20° C.) for 20 min. The MeOH was damped and 50 μL of DPBS containing 1 μg/mL Hochst was added into the cell plates. The intensity of EGFP was quantitated by using OPERA PHENIX® or Operetta™ high content image system (Perkin Elmer) with 20× Water Objective and five field per well. The ratio of EGFP fluorescent intensity in nuclear over cytosol was analyzed using a 4-parameter nonlinear logistic equation to determine the potency of AhR agonists.

Table 10 shows the hAHR nuclear translocation assay EC$_{50}$ values for the exemplified compounds.

TABLE 10 hAHR nuclear translocation assay EC$_{50}$ values

| Example | EC$_{50}$ (nM) |
|---|---|
| 1 | 9.78 |
| 2 | 9.78 |
| 3 | 0.340 |
| 4 | 1.82 |
| 5 | 16.9 |
| 6 | 4.57 |
| 7 | 8.26 |
| 8 | 1.42 |
| 9 | 191 |
| 10 | 13.7 |
| 11 | 64.7 |
| 12 | 7.90 |
| 13 | 4.67 |
| 14 | 26.8 |
| 15 | 1.93 |
| 16 | 1.35 |
| 17 | 1.34 |
| 18 | 1.32 |
| 19 | 1.04 |
| 20 | 5.23 |
| 21 | 4.72 |
| 22 | 4.10 |
| 23 | 11.5 |
| 24 | 2.45 |
| 25 | 1.91 |
| 26 | 2.87 |
| 27 | 6.41 |
| 28 | 3.68 |
| 29 | 2.23 |
| 30 | 1.62 |
| 31 | 2.40 |
| 32 | 0.845 |
| 33 | 2.64 |
| 34 | 7.46 |
| 35 | 4.42 |
| 36 | 2.78 |
| 37 | 1.97 |
| 38 | 1.01 |
| 39 | 0.378 |
| 40 | 2.37 |
| 41 | 2.65 |
| 42 | 9.41 |
| 43 | 0.973 |
| 44 | 2.38 |
| 45 | 16.2 |
| 46 | 31.5 |
| 47 | 0.803 |
| 48 | 11.3 |
| 49 | 2.03 |
| 50 | 8.27 |
| 51 | 4.35 |
| 52 | 6.40 |
| 53 | 0.607 |
| 54 | 0.566 |
| 55 | 0.691 |
| 56 | 2.44 |
| 57 | 1.83 |
| 58 | 3.59 |
| 59 | 3.59 |
| 60 | 396 |
| 61 | 42.0 |
| 62 | 1.84 |
| 63 | 2.55 |
| 64 | 1.54 |
| 65 | 1.22 |
| 66 | 0.525 |
| 67 | 0.500 |
| 68 | 0.137 |
| 69 | 0.161 |
| 70 | 0.961 |
| 71 | 0.189 |
| 72 | 1.79 |
| 73 | 0.275 |
| 74 | 19.0 |
| 75 | 17.7 |
| 76 | 1.12 |
| 77 | 3.49 |
| 78 | 0.297 |
| 79 | 20.3 |
| 80 | 10.9 |
| 81 | 0.574 |
| 82 | 25.1 |
| 83 | 233 |
| 84 | 8.67 |
| 85 | 4.1 |
| 86 | 7.79 |
| 87 | 27.3 |
| 88 | 0.897 |
| 89 | 2.33 |
| 90 | 2.89 |
| 91 | 4.86 |
| 92 | 1.44 |
| 93 | 1.06 |
| 94 | 0.533 |
| 95 | 1.21 |
| 96 | 0.600 |
| 97 | 0.709 |
| 98 | 0.342 |
| 99 | 2.12 |
| 100 | 2.17 |
| 101 | 6.01 |
| 102 | 2.59 |
| 103 | 27.0 |
| 104 | 0.502 |
| 105 | 0.640 |
| 106 | 25.9 |
| 107 | 108 |
| 108 | 2.50 |
| 109 | 1.04 |
| 110 | 2.27 |
| 111 | 10.3 |
| 112 | 0.865 |
| 113 | 11.2 |
| 114 | 2.44 |
| 115 | 2.96 |

The results of this assay demonstrate that the exemplified compounds are AhR agonists.

We claim:
1. A compound of the formula:

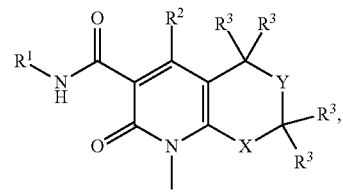

wherein,
R$^1$ is selected from phenyl, C$_1$-C$_6$ alkyl, C$_3$-C$_6$ cycloalkyl, 5- to 6-membered heteroaryl optionally substituted by 1 to 2 R$^i$ and 8- to 10-membered bicyclic heteroaryl optionally substituted with 1 to 2 R$^i$;
R$^2$ is selected from H and OH;
X is selected from bond, —C(R$^3$)$_2$— and —C(R$^3$)$_2$C(R$^3$)$_2$—;
Y is selected from —C(R$^3$)$_2$—, —O— and —N(R$^j$)—;
R$^3$ is independently selected from H and C$_1$-C$_3$ alkyl;
R$^i$ is selected from halogen, CH$_3$, OCH$_3$ and CF$_3$;
R$^j$ is C$_1$-C$_3$ alkyl,
or a pharmaceutically acceptable salt thereof.

2. The compound according to claim 1, wherein $R^1$ is selected from phenyl and 5- to 6-membered heteroaryl optionally substituted with 1 to 2 $R^t$, or a pharmaceutically acceptable salt thereof.

3. The compound according to claim 1, wherein Y is —C($R^3$)$_2$—, or a pharmaceutically acceptable salt thereof.

4. The compound according to claim 1, wherein $R^3$ is independently selected from H, $CH_3$, $CH_2CH_3$ and $CH(CH_3)_2$ or a pharmaceutically acceptable salt thereof.

5. The compound according to claim 1, wherein X is bond, or a pharmaceutically acceptable salt thereof.

6. The compound according to claim 1, which is selected from:

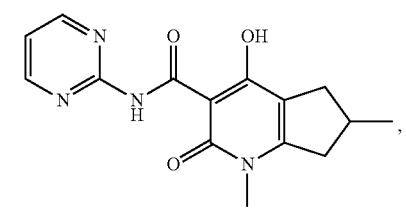

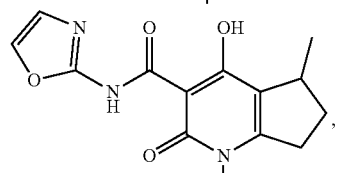

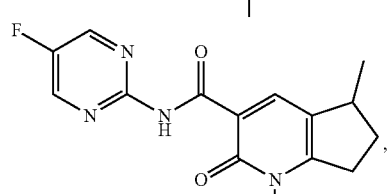

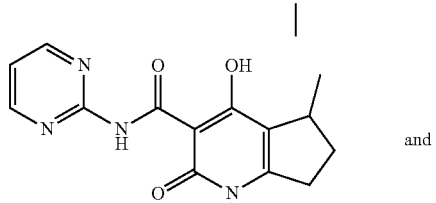

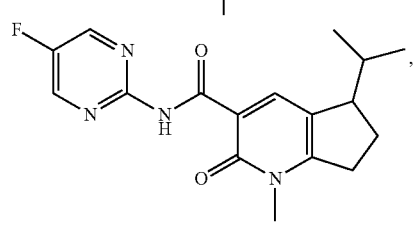

or a pharmaceutically acceptable salt thereof.

7. The compound according to claim 1, which is selected from

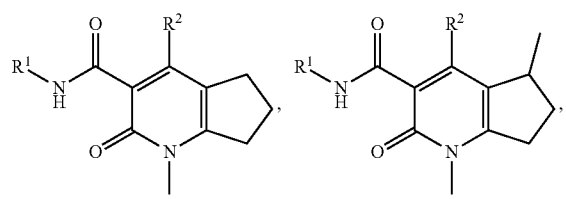

-continued

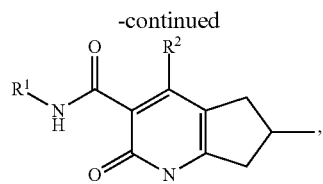

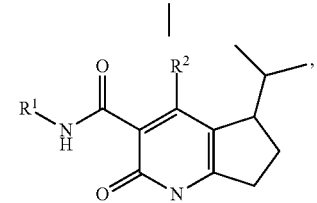

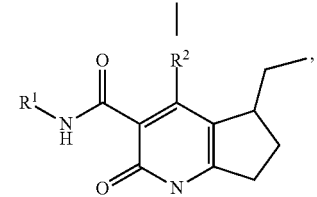

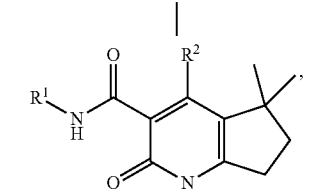

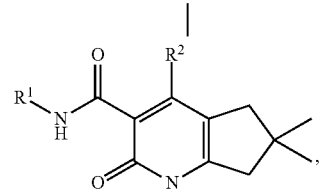

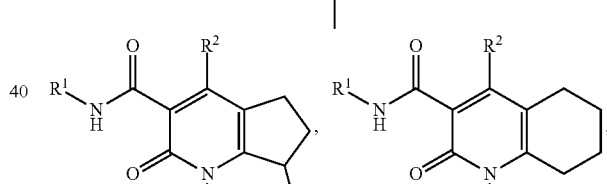

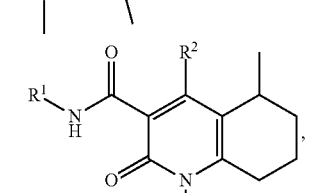

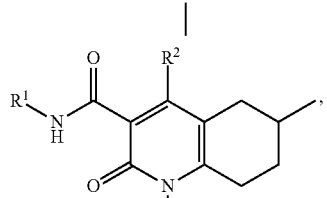

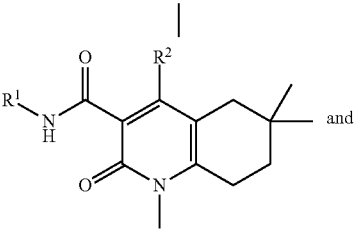

-continued

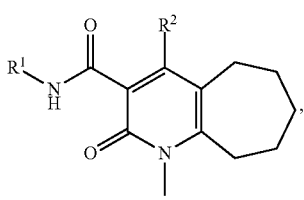

or a pharmaceutically acceptable salt thereof.

8. The compound according to claim 1, which is selected from

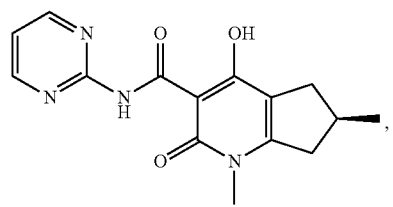

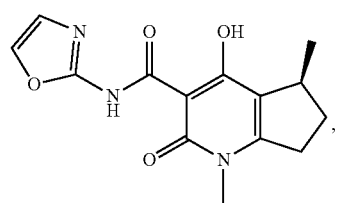

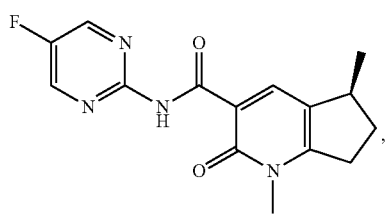

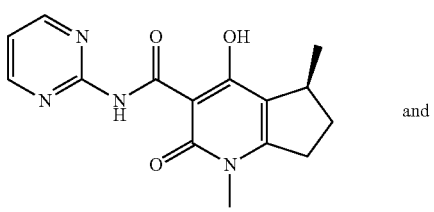

and

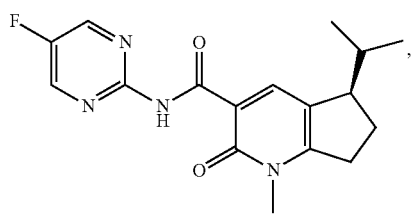

or a pharmaceutically acceptable salt thereof.

9. The compound according to claim 1, which is selected from

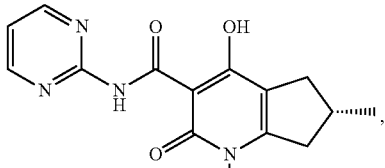

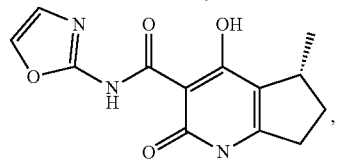

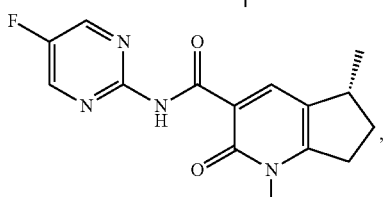

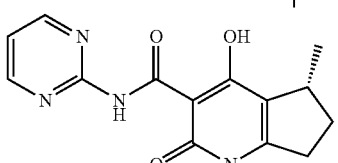 and

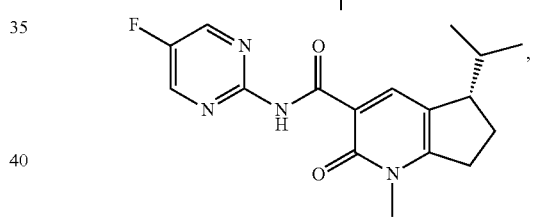

or a pharmaceutically acceptable salt thereof.

10. The compound according to claim 1, which is a free base.

11. A pharmaceutical composition, comprising a compound or a pharmaceutically acceptable salt thereof according to claim 1 with one or more pharmaceutically acceptable carriers, diluents, or excipients.

12. A method of treating a disease or disorder selected from psoriasis, ulcerative colitis, Crohn's disease, graft-versus-host disease and multiple sclerosis in a patient, comprising administering to a patient in need of such treatment an effective amount of a compound of claim 1.

13. A method of treating psoriasis in a patient, comprising administering to a patient in need of such treatment an effective amount of a compound of claim 1.

14. A method of treating ulcerative colitis in a patient, comprising administering to a patient in need of such treatment an effective amount of a compound of claim 1.

15. A method of treating Crohn's disease in a patient, comprising administering to a patient in need of such treatment an effective amount of a compound of claim 1.

16. A method of treating graft-versus-host disease in a patient, comprising administering to a patient in need of such treatment an effective amount of a compound of claim 1.

17. A method of treating multiple sclerosis in a patient, comprising administering to a patient in need of such treatment an effective amount of a compound of claim 1.

\* \* \* \* \*